(12) United States Patent
Sato et al.

(10) Patent No.: US 10,565,895 B2
(45) Date of Patent: Feb. 18, 2020

(54) MOTION ANALYSIS METHOD, MOTION ANALYSIS APPARATUS, AND STORAGE DEVICE

(71) Applicant: SEIKO EPSON CORPORATION, Tokyo (JP)

(72) Inventors: Masafumi Sato, Hara-mura (JP); Toshihiko Kano, Minowa-machi (JP); Kenya Kodaira, Azumino (JP); Kazuo Nomura, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 681 days.

(21) Appl. No.: 15/040,470

(22) Filed: Feb. 10, 2016

(65) Prior Publication Data
US 2016/0236059 A1 Aug. 18, 2016

(30) Foreign Application Priority Data
Feb. 12, 2015 (JP) ................. 2015-025693

(51) Int. Cl.
*G09B 19/00* (2006.01)
*A61B 5/00* (2006.01)
*A61B 5/11* (2006.01)

(52) U.S. Cl.
CPC ........ *G09B 19/0038* (2013.01); *A61B 5/1121* (2013.01); *A61B 5/6895* (2013.01); *A61B 5/742* (2013.01)

(58) Field of Classification Search
CPC ............ A63B 69/3685; G06Q 10/0639; G09B 19/0038; A61B 5/1121; A61B 5/6895
See application file for complete search history.

(56) References Cited

U.S. PATENT DOCUMENTS

| | | |
|---|---|---|
| 6,530,848 B2 | 3/2003 | Gillig |
| 7,128,660 B2 | 10/2006 | Gillig |
| 7,854,667 B2 | 12/2010 | Gillig |
| 8,142,300 B2 | 3/2012 | Iwatsubo et al. |
| 8,142,308 B2 | 3/2012 | Gillig |
| 8,758,151 B2 | 6/2014 | Kimizuka et al. |
| 2003/0144074 A1 | 7/2003 | Gillig |
| 2007/0135225 A1* | 6/2007 | Nieminen .......... A63B 24/0006 473/212 |
| 2012/0316005 A1 | 12/2012 | Shibuya |
| 2014/0114453 A1* | 4/2014 | Bentley ................ A61B 5/1122 700/91 |

(Continued)

FOREIGN PATENT DOCUMENTS

| | | |
|---|---|---|
| JP | 2008-073210 A | 4/2008 |
| JP | 2009-005760 A | 1/2009 |

(Continued)

OTHER PUBLICATIONS

Espace Machine Translation of KR100777598B1.*

*Primary Examiner* — James S. McClellan
*Assistant Examiner* — Peter J Iannuzzi
(74) *Attorney, Agent, or Firm* — Oliff PLC

(57) ABSTRACT

A motion analysis apparatus includes a swing width analysis unit that specifies a swing width from a first position to a second position on a swing trajectory on the basis of coordinates of a swing position of an exercise appliance which are acquired by using an output signal from an inertial sensor in a calculation processing circuit.

25 Claims, 29 Drawing Sheets

(56) References Cited

U.S. PATENT DOCUMENTS

2015/0283427 A1    10/2015   Shibuya

FOREIGN PATENT DOCUMENTS

| JP | 2010-167292 | A |   | 8/2010 |
|----|-------------|---|---|--------|
| JP | 2012-196241 | A |   | 10/2012 |
| JP | 2012-223232 | A |   | 11/2012 |
| JP | 2012-254206 | A |   | 12/2012 |
| JP | 2013-138758 | A |   | 7/2013 |
| JP | 2014-117519 | A |   | 6/2014 |
| KR | 100777598   | B1 | * | 11/2007 |

* cited by examiner

| GyroZ (rad/s) | HITTING POINT MEASUREMENT VALUE (mm) |
|---|---|
| −114.6 | 8 |
| 186.9 | −7 |
| 194.1 | −8 |
| −259.6 | 18 |
| −263.4 | 12 |
| 186.0 | −7 |
| −197.4 | 10 |
| 126.7 | −5 |
| 83.5 | −2 |
| −106.0 | 13 |
| 202.3 | −16 |
| −248.8 | 25 |
| −97.2 | 10 |

MOTION ANALYSIS METHOD, MOTION ANALYSIS APPARATUS, AND STORAGE DEVICE

BACKGROUND

1. Technical Field

The present invention relates to a motion analysis method, a motion analysis apparatus, and a storage device.

2. Related Art

JP-A-2008-73210 has proposed a motion analysis apparatus in which an inertial sensor including a three-axis acceleration sensor and a three-axis gyro sensor is attached to an exercise appliance, for example, a golf club, and a swing is analyzed by using an output signal from the inertial sensor. If the apparatus is used, convenience is improved since a camera is not necessary.

In sports with hitting, such as golf or baseball, there is a case where the distance by which a hit ball is moved is adjusted. Meanwhile, especially, when a golf putter is used among golf clubs, the perception of distance from an address position to a cup is necessary in order to drop a ball in the cup.

However, there is a problem in that a distance cannot be estimated in a motion analysis apparatus using an inertial sensor.

SUMMARY

An advantage of some aspects of the invention is to provide a motion analysis method and a motion analysis apparatus capable of estimating a distance by using an inertial sensor, and a storage device.

(1) An aspect of the invention relates to a motion analysis method including specifying a swing width from a first position to a second position on a swing trajectory on the basis of a swing position of an exercise appliance which is acquired by using an output signal from an inertial sensor.

According to the aspect of the invention, in light of an arrival point of a hit ball and a swing width of the exercise appliance being associated with each other, a swing width from the first position to the second position on a motion trajectory of the exercise appliance is specified. A user checks a swing width for each swing motion of the exercise appliance, and can thus gain accuracy of reproducing a swing width of the exercise appliance corresponding to a traveled distance of a hit ball.

(2) In the aspect of the invention, the first position may be a swing start position, and the second position may be a swing turning position. In this case, a swing width from the first position to the second position is a swing width at taking-back (backswing). This swing width can directly influence the distance by which a hit ball is moved, and thus, it is possible to gain an accurate perception of distance, for example, during half swing of a golf putter or a golf iron by learning a swing width during a backswing.

(3) In the aspect of the invention, the first position may be a swing turning position, and the second position may be a hitting position. In this case, a swing width from the first position to the second position is a swing width at a downswing, and is substantially the same as a swing width at taking-back (backswing). This swing width can directly influence the distance by which a hit ball is moved, and thus, it is possible to gain an accurate perception of distance by learning a swing width at a downswing.

(4) In the aspect of the invention, the first position may be a hitting position, and the second position may be a swing end position. In this case, a swing width from the first position to the second position is a swing width of follow-through. Since there is a correlation in that a swing width of follow-through increases as a swing width of a backswing increases, it is possible to gain an accurate perception of distance by learning a swing width of follow-through.

(5) In the aspect of the invention, the first position may be a swing turning position, and the second position may be a swing end position. In this case, a swing width from the first position to the second position is the total swing width at downswing and follow-through. The swing width has a correlation with a swing width of a backswing which directly influences the perception of distance, and thus it is possible to gain an accurate perception of distance by learning a total swing width of a downswing and follow-through.

(6) In the aspect of the invention, the first position may be a stoppage position when a swing is started, and the second position may be a swing end position. In this case, a swing width from the first position to the second position is the entire swing width. The swing width has a correlation with a swing width at a backswing, and thus, it is possible to gain an accurate perception of distance, for example, during half swing of a golf putter or a golf iron by learning the entire swing width at a swing.

(7) In the aspect of the invention, the swing width may be the length of the swing trajectory from the first position to the second position. For example, regarding a plurality of position coordinates on the swing trajectory of the exercise appliance, a distance between position coordinates adjacent to each other is integrated on the basis of an output signal from the inertial sensor, and thus, it is possible to obtain a swing width of a route from the first position to the second position.

(8) In the aspect of the invention, the swing width may be the length obtained by projecting the swing trajectory from the first position to the second position onto a projection plane. For example, it is possible to obtain a swing width from the first position to the second position by obtaining a distance between coordinates of the first position and the second position projected onto a projection plane.

(9) In the aspect of the invention, images indicating the exercise appliance may be displayed at a plurality of positions on the swing trajectory of the exercise appliance from the first position to the second position. Consequently, it is possible to visually recognize a swing width of the exercise appliance.

(10) In the aspect of the invention, a display pitch of the images displayed at the plurality of positions may be short in a period in which a swing speed is high, and may be long in a period in which the swing speed is low. Consequently, it is possible to visually recognize both a swing width and a swing speed of the exercise appliance.

(11) In the aspect of the invention, the images displayed at the plurality of positions may be sequentially displayed in synchronization with swing movement according to the swing movement of the exercise appliance. Consequently, it is possible to dynamically visually recognize a swing width of the exercise appliance.

(12) In the aspect of the invention, variation in the swing width may be displayed. The variation in the swing width may be calculated by using, for example, a standard deviation. A statistical value indicating the variation in the swing width is displayed, and thus, it is possible to estimate reproducibility of a swing width of the exercise appliance corresponding to a traveled distance of a hit ball.

(13) Another aspect of the invention relates to a motion analysis apparatus including an analysis unit that specifies a swing width from a first position to a second position on a swing trajectory on the basis of a swing position of an exercise appliance which is acquired by using an output signal from an inertial sensor. The apparatus of the invention can appropriately perform the above-described method of the invention.

(14) Still another aspect of the invention relates to a storage device storing a motion analysis program causing a computer to execute specifying a swing width from a first position to a second position on a swing trajectory on the basis of a swing position of an exercise appliance which is acquired by using an output signal from an inertial sensor, in which the first position is a swing start position, and the second position is a swing turning position. The program according to the aspect may be built into the storage device of the motion analysis apparatus performing the method according to the invention, or may be installed to the storage device of the motion analysis apparatus from a server or a storage medium.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described with reference to the accompanying drawings. The embodiment described below are not intended to improperly limit the content of the invention, and all constituent elements described in the present embodiment are not essential as solving means of the invention.

(1) Configuration of Golf Club Analysis Apparatus

Figure 1:
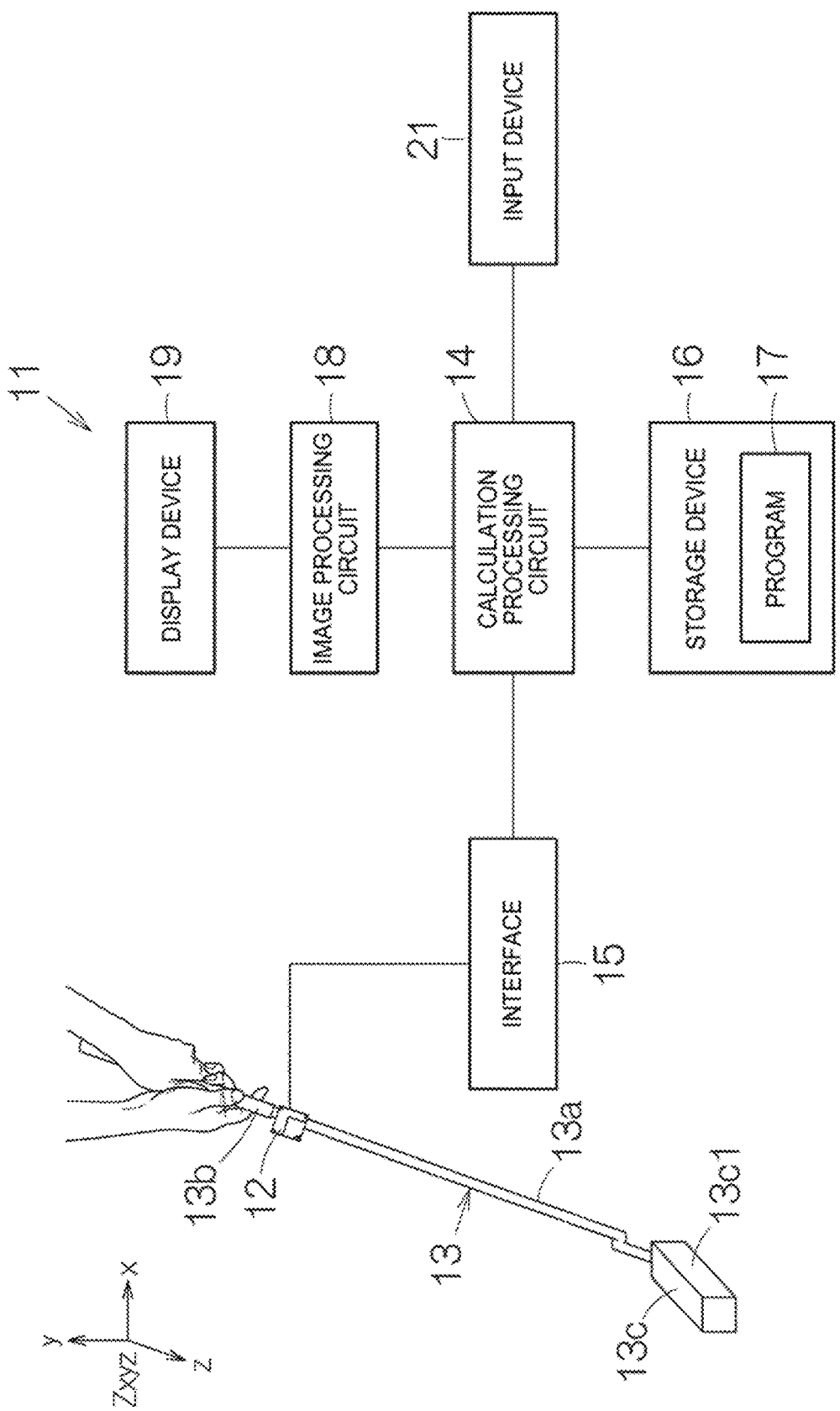
FIG. 1 is a conceptual diagram schematically illustrating a configuration of a golf swing analysis apparatus according to an embodiment of the invention.

FIG. 1 schematically illustrates a configuration of a golf swing analysis apparatus (motion analysis apparatus) 11 according to an embodiment of the invention. The golf swing analysis apparatus 11 includes, for example, an inertial sensor 12. An acceleration sensor and a gyro sensor are incorporated into the inertial sensor 12. The acceleration sensor can detect separate acceleration in three-axis directions which are perpendicular to each other. The gyro sensor can detect separate angular velocity around each of three axes (x, y, and z) which are perpendicular to each other. The inertial sensor outputs a detection signal. Acceleration and angular velocity are specified in each axis by the detection signal. The acceleration sensor and the gyro sensor detect information regarding acceleration and angular velocity with relatively high accuracy. The inertial sensor 12 is attached to a golf club (exercise appliance) 13. The golf club, for example, a golf putter 13 includes a shaft 13a and a grip 13b. The grip 13b is gripped with the hands. The grip 13b is formed on the same axis as an axis of the shaft 13a. A club head 13c is coupled to a tip of the shaft 13a. Preferably, the inertial sensor 12 is attached to the shaft 13a or the grip 13b of the golf club 13. The inertial sensor 12 may be fixed to the golf club 13 so as not to be relatively moved.

Here, when the inertial sensor 12 is attached, one (z axis) of detection axes of the inertial sensor 12 matches the axis of the shaft 13a. Another detection axis (x axis) of the inertial sensor 12 matches a direction in which a direction (face normal direction) perpendicular to a face surface (hitting surface) 13c1 is projected on a horizontal plane in a state in which a sole (grounding surface) of the club head 13c is made horizontal. The face surface is not limited to a vertical surface, and is inclined with respect to the vertical surface, and thus the x axis is set in the direction in which the face normal direction is projected onto a horizontal surface. The y axis is perpendicular to the x axis and the z axis. A sensor coordinate system Σxyz is defined by the x axis, the y axis, and the z axis.

The golf swing analysis apparatus 11 includes a calculation processing circuit 14. The calculation processing circuit 14 is connected to the inertial sensor 12. A predetermined interface circuit 15 is connected to the calculation processing circuit 14. In connection, the interface circuit 15 may be connected to the inertial sensor 12 in a wired manner, and may be connected to the inertial sensor 12 in a wireless manner. A detection signal is supplied to the calculation processing circuit 14 from the inertial sensor 12.

The calculation processing circuit 14 is connected to a storage device 16. The storage device 16 can store, for example, a golf swing analysis software program (motion analysis program) 17 and related data. The calculation processing circuit 14 realizes a golf swing analysis method by executing the golf swing analysis software program 17. The storage device 16 may include a dynamic RAM (DRAM), a large capacity storage device unit, a nonvolatile memory, and the like. For example, when a golf swing analysis method is performed, the golf swing analysis software program 17 is downloaded from, for example, a server and is temporarily held in the DRAM. Alternatively, the golf swing analysis software program 17 may be preserved in the large capacity storage device unit such as a hard disk drive (HDD) along with data. The nonvolatile memory stores a program or data with a relatively small capacity, such as a basic input/output system (BIOS).

The storage device 16 stores club specification information indicating a specification of the golf club 13, sensor attachment position information, and the like. For example, a user operates an input device 21 and sequentially inputs type numbers of the golf club 13 to be used (alternatively, selects a type number from a type number list) so that specification information (for example, information regarding the length of the shaft, a central position, a face angle, and a loft angle) for each type number is stored in the storage device 16 in advance. In this case, specification information of an input type number is used as the club specification information. Alternatively, the sensor unit 12 may be attached at a predetermined position (for example, a distance of 20 cm from the grip) which is set so that information regarding the predetermined position is stored as the sensor attachment position information in advance. As exercise conditions, for example, in a case of a golf putter, a distance from an address position to a cup, a size of the cup, and speed on the turf are stored in the storage device 16 via the input device 21.

The calculation processing circuit 14 is connected to an image processing circuit 18. The calculation processing circuit 14 sends predetermined image data to the image processing circuit 18. The image processing circuit 18 is connected to a display device 19. In connection, the image processing circuit 18 is connected to a predetermined interface circuit (not illustrated). The image processing circuit 18 sends an image signal to the display device 19 on the basis of input image data. An image specified by the image signal is displayed on a screen of the display device 19. The calculation processing circuit 14 or the image processing circuit 18 can convert a coordinate space of the sensor coordinate system Σxyz into an absolute reference coordinate system ΣXYZ (for example, an X-Z plane is a horizontal plane, and an X-Y plane is a vertical plane) which is a real space (three-dimensional space). The display device 19 employs a liquid crystal display or other flat panel displays, and displays a three-dimensional image or a two-dimensional image in the absolute reference coordinate system ΣXYZ. Here, the calculation processing circuit 14, the storage device 16, and the image processing circuit 18 are provided as, for example, a computer device.

The calculation processing circuit 14 is connected to the input device 21. The input device 21 includes at least alphabet keys and numerical keys. Text information or numerical value information is input to the calculation processing circuit 14 from the input device 21. The input device 21 may be constituted of, for example, a keyboard. The combination of the display device, the computer device, and the keyboard may be replaced with a portable terminal such as a smart phone or a tablet PC.

(2) Outline of Calculation Processing Circuit

Figure 2:
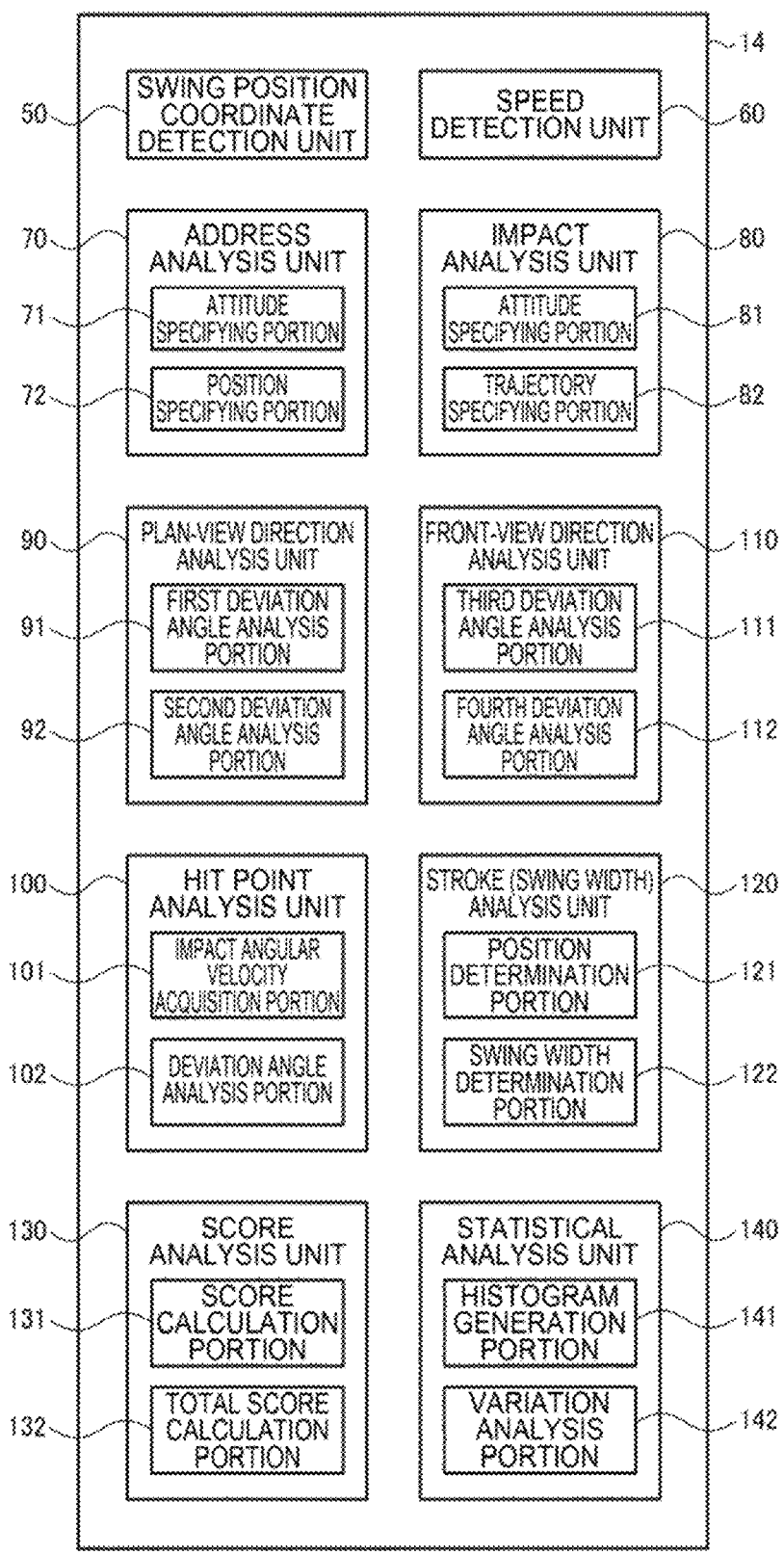
FIG. 2 is a block diagram schematically illustrating a configuration of a calculation processing circuit according to the embodiment of the invention.

FIG. 2 schematically illustrates a configuration of the calculation processing circuit 14 according to the embodiment. The calculation processing circuit 14 may include a swing position coordinate detection unit 50, a speed detection unit 60, an address (stoppage) analysis unit 70, an impact analysis unit 80, a plan-view direction analysis unit 90, a hit point analysis unit 100, a front-view direction analysis unit 110, a stroke analysis unit (swing width analysis unit) 120, a score analysis unit 130, and a statistical analysis unit 140, and the like. At least one of the analysis units 90 to 120 may be omitted according to a grade of the motion analysis apparatus.

The swing position coordinate detection unit 50 detects coordinates of the club head 13c during a swing from a swing start position (address position) to a swing end position (finish position) through a swing turning position (top position) and a hitting position (impact virtual vertical plane position).

Figure 4A:
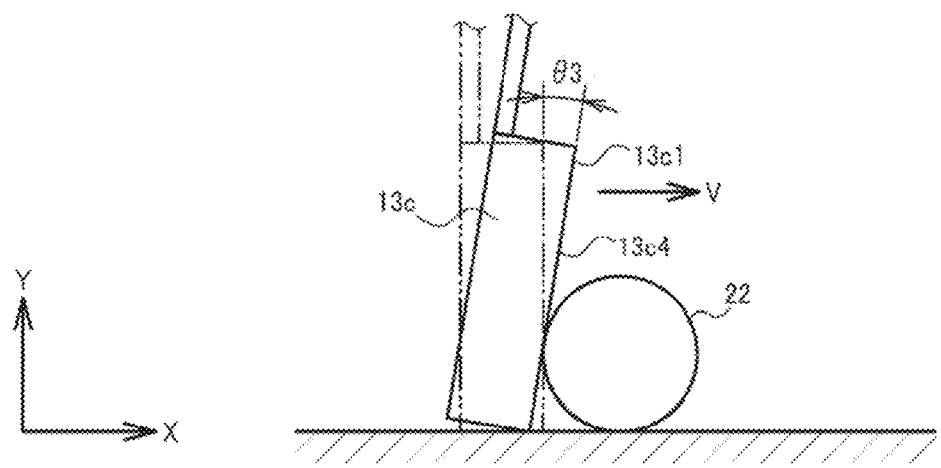
FIG. 4A is a diagram illustrating a third deviation angle (delta-loft angle) and an impact speed.
Figure 4B:
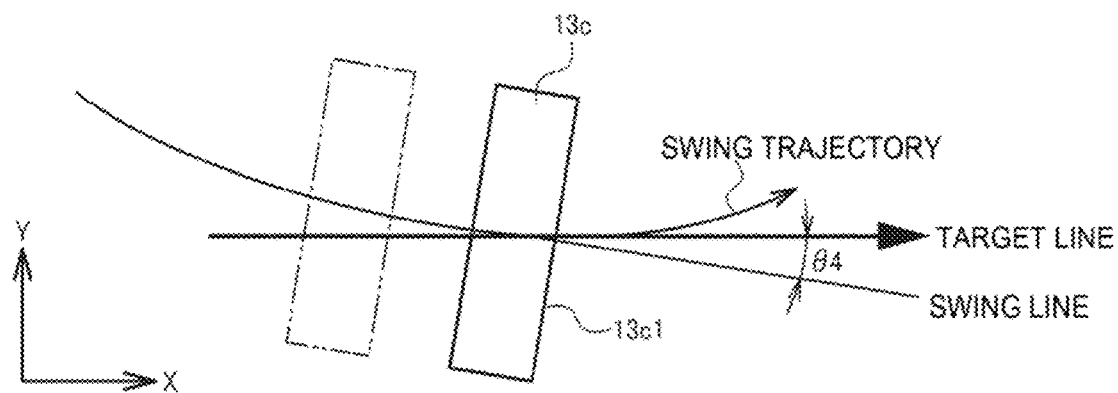
FIG. 4B is a diagram illustrating a fourth deviation angle (attack angle).

The speed detection unit 60 detects a speed V of the club head 13c, for example, during impact by using an output signal from the inertial sensor 12 (refer to FIG. 4B). The address analysis unit 70 analyzes an attitude or a position of the face surface 13c1 of the club head 13c during address (stoppage). The impact analysis unit 80 analyzes an attitude of the face surface 13c1 of the club head 13c during impact, or a trajectory of the face surface 13c1 on the verge of impact.

Figure 3A:
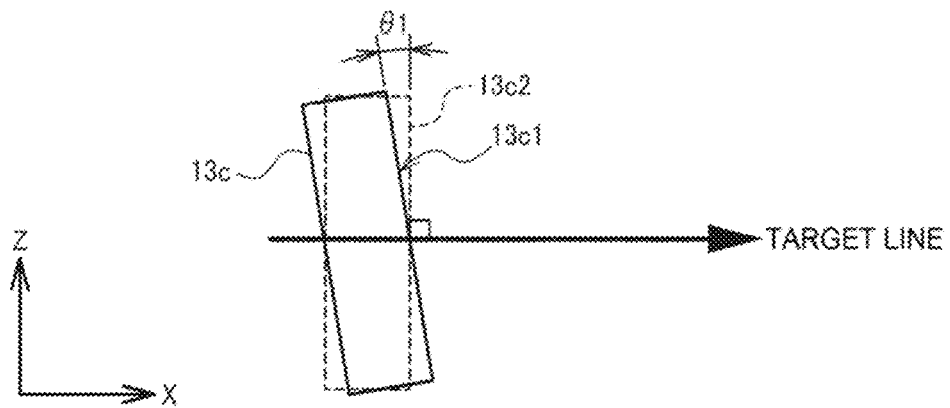
FIG. 3A is a diagram illustrating a first deviation angle (absolute face angle).
Figure 3B:
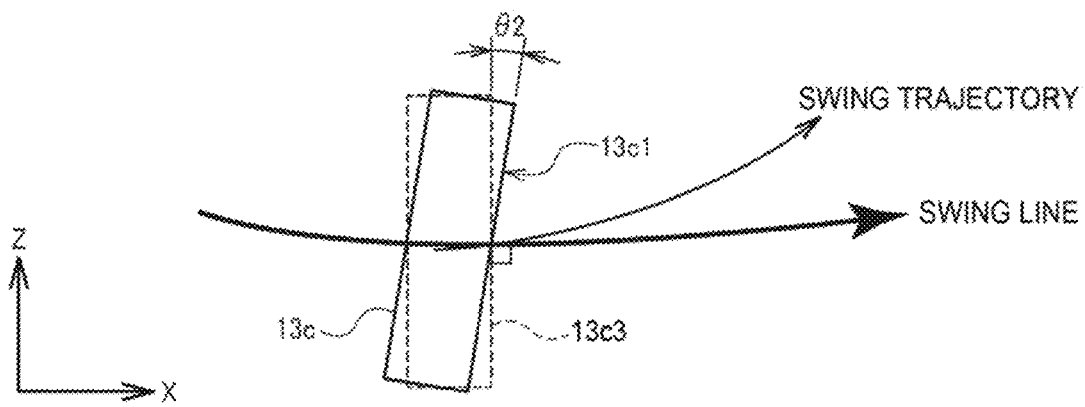
FIG. 3B is a diagram illustrating a second deviation angle (square degree).

The plan-view direction analysis unit 90 analyzes the direction of the club head 13c in a plan view. The plan-view direction analysis unit 90 analyzes at least one of a first deviation angle θ1 (absolute face angle) between the face surface 13c1 during impact and a virtual vertical plane 13c2 with respect to a hitting target direction (a target line direction which is, for example, a direction in which the normal direction of the face surface 13c1 during address is projected onto the X-Z plane) as illustrated in FIG. 3A, and a second deviation angle θ2 (square degree) between the face surface 13c1 during impact and a virtual vertical plane 13c3 with respect to a tangential direction (a swing line direction or a hit ball direction) during impact in contact with a movement trajectory of the face surface 13c1 as illustrated in FIG. 3B.

Figure 3C:
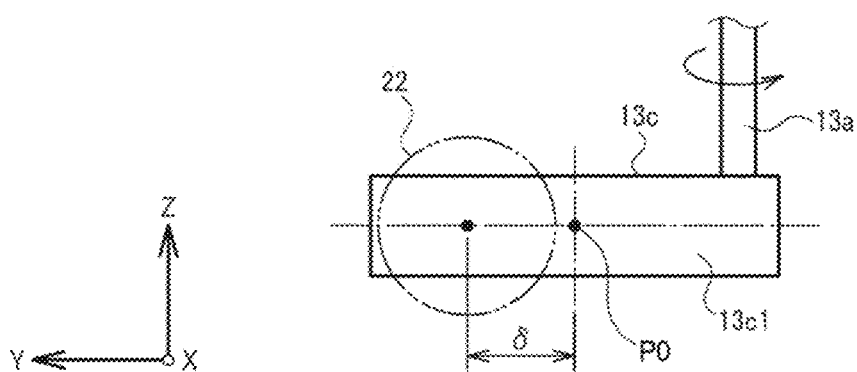
FIG. 3C is a diagram illustrating a deviation amount from a hit point.

The hit point analysis unit 100 analyzes a deviation amount δ of a hit point (hitting position) of a ball 22 during impact relative to a virtual reference position P0 set on the face surface 13c1, on the basis of angular velocity around the shaft 13a, as illustrated in FIG. 3C.

The front-view direction analysis unit 110 analyzes the direction of the club head 13c in a front view of viewing a golfer (a user handling an exercise appliance) from the front side. The front-view direction analysis unit 110 analyzes at least one of a third deviation angle θ3 (delta-loft angle) between an inclined angle (actual loft angle) with respect to the vertical surface of the face surface 13c1 during impact and a reference inclined angle (which is, for example, a loft angle as a standard value of the putter 13 and is illustrated as a substantially vertical surface in FIG. 4A) as illustrated in FIG. 4A, and a fourth deviation angle θ4 (attack angle) between a tangential direction (swing line direction) during impact in contact with the movement trajectory of the face surface 13c1 projected onto the vertical surface and a target direction (hitting target direction) projected onto the vertical surface.

Figure 4C:
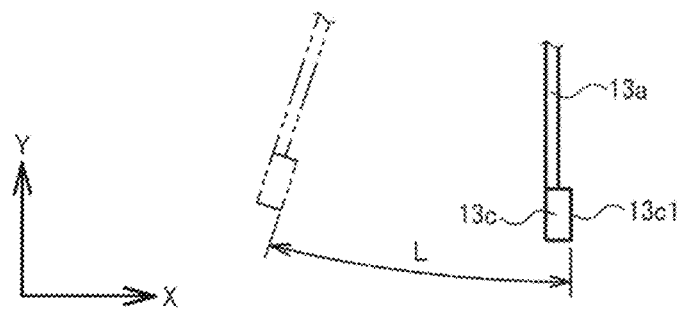
FIG. 4C is a diagram illustrating a swing width.

The stroke analysis unit (swing width analysis unit) 120 specifies a swing width from a first position to a second position on a swing trajectory on the basis of coordinates of the two positions (the first position and the second position) from the swing position coordinate detection unit 50. For example, as illustrated in FIG. 4C, a stroke (swing width) from an address position (first position) to a swing turning position (second position) is analyzed.

As illustrated in FIGS. 3A to 4C, the score analysis unit 130 analyzes a score (performance score) for each of a plurality of swing analysis data items (the deviation angles θ1 to θ4, the deviation amount δ, the swing width L, and the speed V), or a score (comprehensive performance score) which is computed by weighting data selected from the plurality of swing analysis data items. The statistical analysis unit 140 analyzes statistical values (a total number of times, an average value, a standard deviation, and the like) based on the accumulated data for each of the plurality of swing analysis data items.

(3) Display Example in Display Device
(3-1) Initial Screen

Figure 5:
FIG. 5 is a diagram illustrating an initial screen of an analysis screen.

FIG. 5 is a diagram illustrating an example of, for example, an initial screen of swing analysis data displayed on the display device 19. In FIG. 5, an upper part of the initial screen displays respective information pieces such as a user name, the date and time, the type of putter (L-mullet), a distance (10 ft) to a cup, and a speed (Slow) on the turf. The center of the inertial sensor displays, for example, images (a plurality of positions) indicating the putter 13 along a swing trajectory from an address position to a swing turning position. The swing trajectory corresponds to an image projected onto the X-Y plane (vertical plane) of the absolute reference coordinate system. A black triangular mark on the left side under the swing trajectory image region indicates a reproduction button. If the reproduction button is operated, a time seek bar on the right side of the reproduction button moves from the left to the right, and images indicating the putter 13 are sequentially additionally displayed at a plurality of positions according to movement of the putter 13. White triangular marks over the movement region of the time seek bar indicate positions of an address, a top, an impact, and finish in this order from the left side. The time seek bar may be operated and be held and stopped at a position of interest. A performance score (for example, 100 points) analyzed by the score analysis unit 130 is displayed on the left side of the center of the initial screen. A lower part of the initial screen displays Direction (plan-view direction analysis data), Hitpoint (hit point analysis data), Stroke (stroke analysis data), and Rising (front-view direction analysis data) along with analysis data. If any one of four display regions of the lower part of the initial screen is touched, details of selected analysis data are displayed.

(3-2) Screen of Individual Analysis Data
(3-2-1) Direction

Figure 6:
FIG. 6 is a diagram illustrating an analysis screen when "Direction" is selected in FIG. 5.
Figure 7:
FIG. 7 is a diagram illustrating an analysis screen when "FACE" is selected in FIG. 6.

FIGS. 6 to 10 illustrate screen examples which are subsequently displayed when "Direction" is selected on the initial screen. FIG. 7 illustrates an example of a display screen of plan-view direction analysis data in one swing. FIG. 6 is a screen displayed when "Direction" is selected on the initial screen. In FIG. 6, on the basis of analysis data from the plan-view direction analysis unit 90 illustrated in FIG. 2, 3.4 degrees is enlarged and displayed in an emphasized manner as the first deviation angle θ1 (as illustrated in FIG. 3A, a deviation angle (absolute face angle) between the face surface 13c1 during impact and the virtual vertical plane 13c2 with respect to the hitting target direction (target line direction)).

In the screen center of FIG. 6 and FIG. 7 illustrating a screen displayed when "FACE" in FIG. 6 is selected, a hitting direction in which the normal direction to the face surface 13c1 of the putter 13 is projected onto the projection plane (horizontal plane), and a speed of the club head 13c of the putter 13 during impact are displayed in a coordinate system in which the hitting target direction is set. As the coordinate system, for example, a polar coordinate system is displayed. The direction of 0 degrees is the hitting target direction in an angle axis which is one axis of the polar coordinate system. A specified hitting direction is displayed as a line segment extending in a direction which is perpendicular to the face surface 13c1 of the image indicating the club head 13c of the putter 13 in the polar coordinate system. The direction of 0 degrees may be displayed as a hitting direction at all times in the angle axis which is one axis of the polar coordinate system.

An angle in the angle axis of the polar coordinate system is exaggerated to be larger than an actual angle, and, for example, an angle range of ±5 degrees is illustrated to be exaggerated to an angle range of 90 degrees or more. This is so that a deviation of a hitting direction relative to a hitting target direction can be easily viewed. Another axis of the polar coordinate system is a speed axis. An end position of the line segment indicating the hitting direction extending from the face surface of the image indicating the club head 13c of the putter 13 indicates a speed of the club head 13c (the face surface 13c1) during impact.

In the present embodiment, in light of a hitting direction and a speed of the face surface 13c1 during impact being associated with the directionality and the perception of distance of a hit ball, the hitting direction and the speed of the face surface 13c1 during impact are displayed in the same coordinate system. The user checks a deviation of a hitting direction relative to the hitting target direction and a speed during impact for each swing motion of the putter 13, and can thus gain accuracy of reproducing the directionality and the perception of distance of a hit ball. Here, the hitting direction during impact may be set to a direction in which the normal direction to the face surface 13c1 during impact is projected onto the projection plane. Since the face surface 13c1 is not limited to a plane which is parallel to the vertical surface and may be inclined with respect to the vertical surface, the direction in which the normal direction of the face surface 13c1 is projected onto the projection plane (horizontal plane) may be assumed to be a hitting direction. Specifying a hitting direction will be described later, and a hitting direction (a tangential direction during impact with respect to a movement trajectory of the face surface) during impact may be specified on the basis of a movement vector of the face surface 13c1.

The hitting target direction may be specified as a direction in which a normal direction to the face surface 13c1 during address (during stoppage) before starting a swing motion is projected onto the projection plane. The hitting target direction may be a preset known fixed direction, but may be specified on the basis of the direction of the face surface 13c1 during stoppage for each swing motion before starting the swing motion so as to easily recognize a deviation between intended swing and actual swing.

In the image indicating the putter 13 in a plan view, the face surface 13c1 is set to be directed in a hitting direction and is displayed in the polar coordinate system illustrated in FIGS. 6 and 7, and, thus, particularly, a deviation between the direction of the hitting surface and the hitting target direction is visually recognized, thereby allowing the cause of the deviation of the hitting direction to be easily recognized.

In the polar coordinate system illustrated in FIGS. 6 and 7, a target region of, for example, ±1 degree including the hitting target direction (0 degrees) may be displayed so as to be differentiated from other regions. In the above-described way, since a target is a zone rather than a line, a target achievement ratio is increased, the user feels comfortable, and thus an exercise practice effect can be improved. In a case of the putter 13, the target region may be obtained as an angle range from a target line on the basis of a distance L from the address position to the cup center, and a radius R of the cup. For example, if R=5.4 cm, and L=155.4 cm, the target region is ±arcsin (R/L)=±1.9 degrees.

In the polar coordinate system illustrated in FIGS. 6 and 7, coordinate positions (five coordinate positions in FIGS. 6 and 7) defined by a hitting direction and a speed specified in the past may be displayed so as to be differentiated from coordinate positions defined by a hitting direction and a speed specified this time. In the above-described manner, in a case where exercise is repeatedly performed, the achievement of a practice effect can be visually recognized.

Figure 8:
FIG. 8 is a diagram illustrating an analysis screen when "Histogram" is selected in FIG. 5 or 6.

If "Histogram" on the lower left in FIG. 6 or FIG. 7 is selected, the screen of FIG. 6 or 7 is changed to a screen of FIG. 8. A screen lower part illustrated in FIG. 8 displays a histogram indicating, for example, a distribution of hitting directions on the basis of analysis data from the statistical analysis unit 140 illustrated in FIG. 2. As illustrated in FIG. 8, a position of a hitting direction measured this time may also be displayed in the histogram.

Figure 9:
FIG. 9 is a diagram illustrating an analysis screen when "SQUARE" is selected in FIGS. 6 to 8.

In FIGS. 6 to 8, if the column "SQUARE" on the screen upper right is selected, the screen is changed to a screen of FIG. 9. In FIG. 9, −0.2 degrees is enlarged and displayed in an emphasized manner as the second deviation angle θ2 (square degree: refer to FIG. 3B) of the club head 13c during impact on the basis of analysis data from the plan-view direction analysis unit 90 illustrated in FIG. 2 in the column "SQUARE" on the screen upper right. At the screen center of FIG. 8, the angle axis of the polar coordinate system is changed to an angle axis of the square degree θ2. A position of the square degree θ2=0 in the angle axis of the polar coordinate system becomes a target direction. In FIG. 9, a normal line to the face surface of the image indicating the putter 13 is displayed at the position of the square degree θ2=−0.2 degrees. Also in this case, as illustrated in FIG. 9, coordinate positions (five coordinate positions in FIG. 9) defined by a square degree and a speed specified in the past may be displayed so as to be differentiated from a coordinate position defined by a square degree and a speed specified this time.

Figure 10:
FIG. 10 is a diagram illustrating an analysis screen when "Histogram" is selected in FIG. 9.

If "Histogram" on the screen lower left of FIG. 9 is selected, the screen of FIG. 9 is changed to a screen of FIG. 10. A screen lower part illustrated in FIG. 10 displays a histogram indicating a distribution of speeds at a square degree on the basis of analysis data from the statistical analysis unit 140 illustrated in FIG. 2, As illustrated in FIG. 10, a position of a square degree measured this time may also be displayed in the histogram.

(3-2-2) Hitpoint

Figure 11:
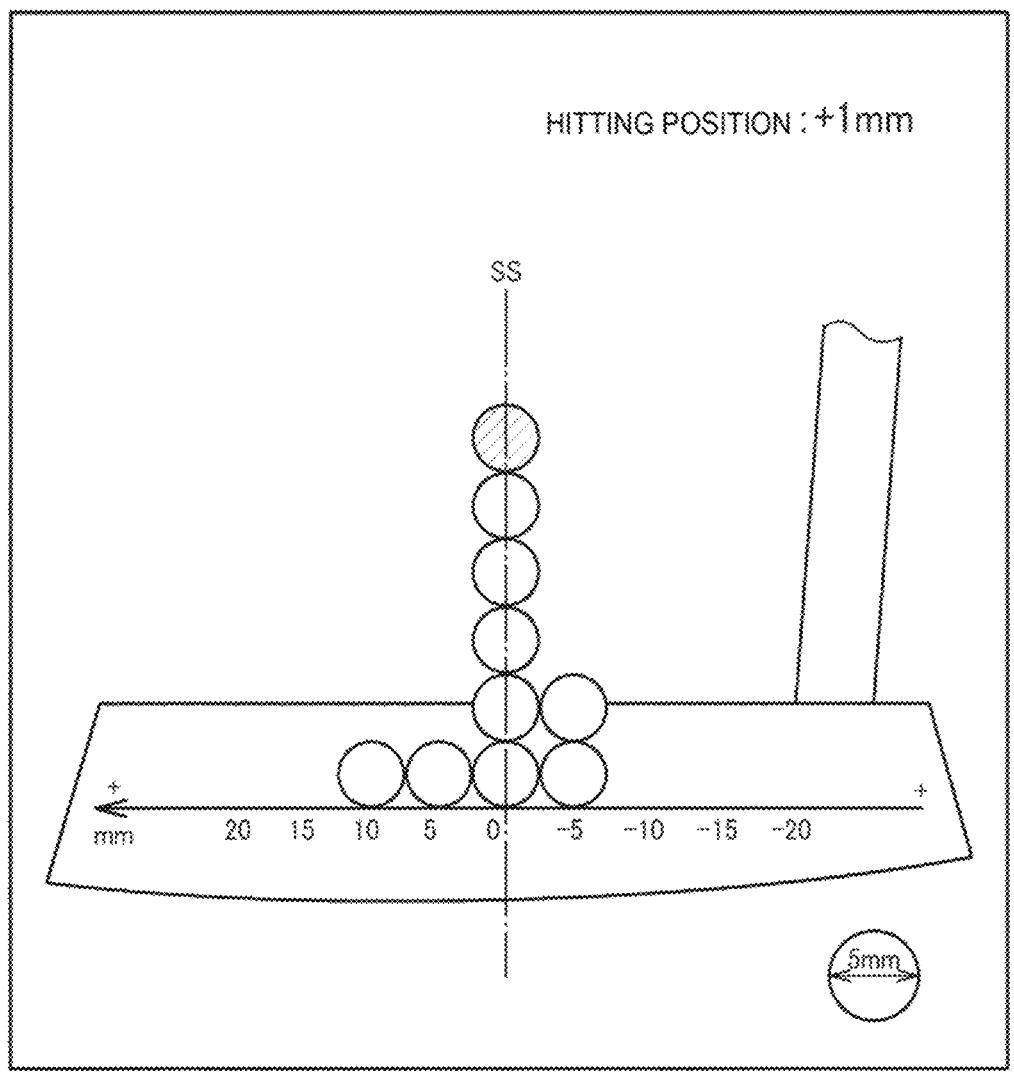
FIG. 11 is a diagram of a display screen illustrating a deviation amount of a hitting position from a sweet spot.

FIG. 11 illustrates apart of a screen displayed when "Hitpoint" is selected on the initial screen. The face surface 13c1 of the club head 13c is displayed on the screen illustrated in FIG. 11, and a dot chain line SS which is a vertical line in FIG. 11 indicates a sweet spot of the golf club 13.

Circular marks illustrated in FIG. 11 indicate hitting positions of balls at ten swings. A diameter of a single circular mark in the horizontal direction indicates a width of a position where the ball is hit, and is a width of "5 mm" in the example illustrated in FIG. 11. In other words, the number of circular marks located on the same vertical line indicates a frequency of hitting positions of balls. For example, in the example illustrated in FIG. 11, it can be seen that a frequency of the hitting position "−5±2.5 (mm)" is "twice".

A circular mark indicated by diagonal lines indicates the most recent hitting position of a ball. In the example illustrated in FIG. 11, the most recent position of the ball is "+1 mm", and the circular mark indicated by the diagonal lines is displayed in a grade of "0±2.5 (mm)". Also regarding a hit point, "Histogram" may be selected, and thus the same histogram as in FIG. 8 or FIG. 10 may be displayed.

(3-2-3) Stroke

Figure 12:
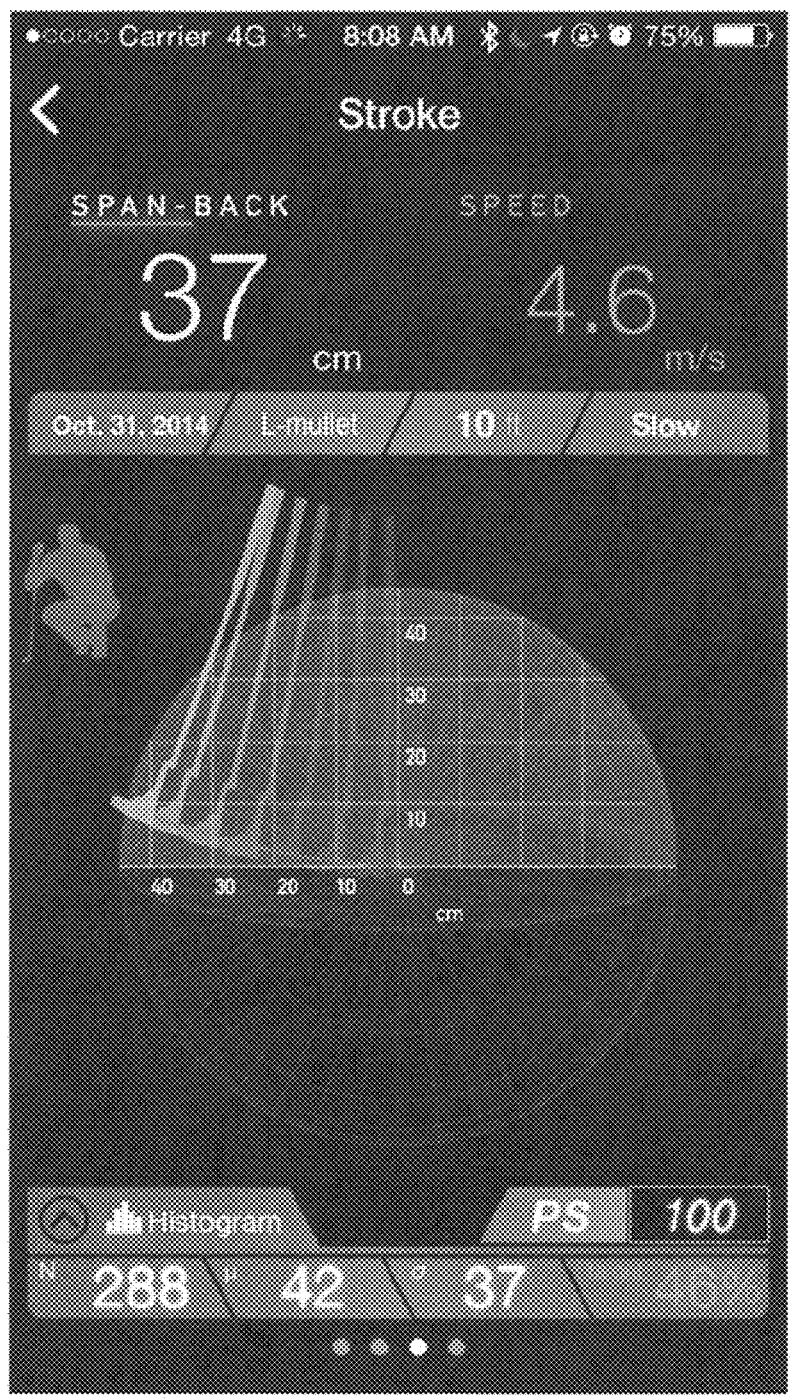
FIG. 12 is a diagram illustrating an analysis screen when "Stroke" is selected in FIG. 5.
Figure 13:
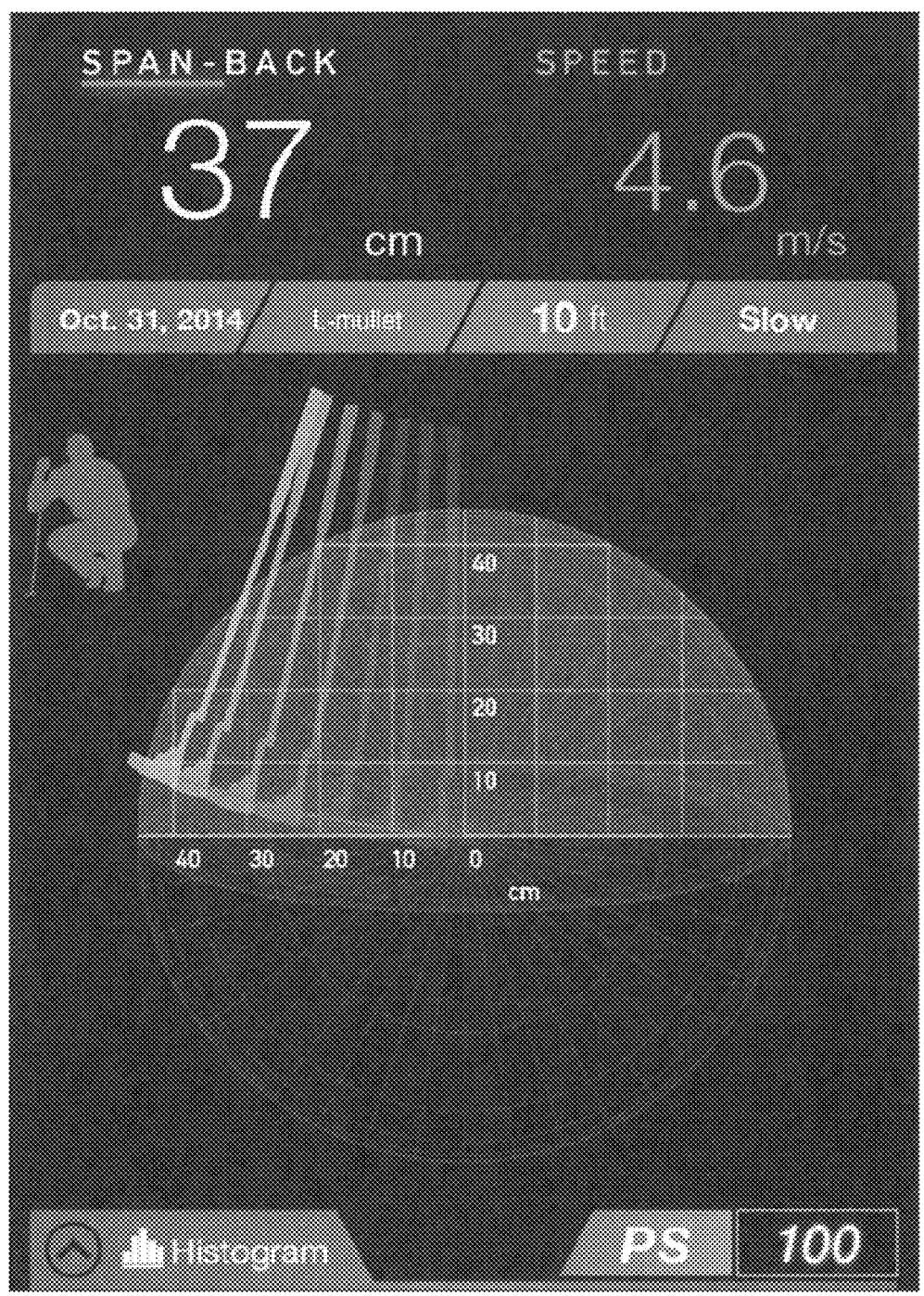
FIG. 13 is a diagram illustrating an analysis screen when "SPAN-BACK" is selected in FIG. 12.
Figure 14:
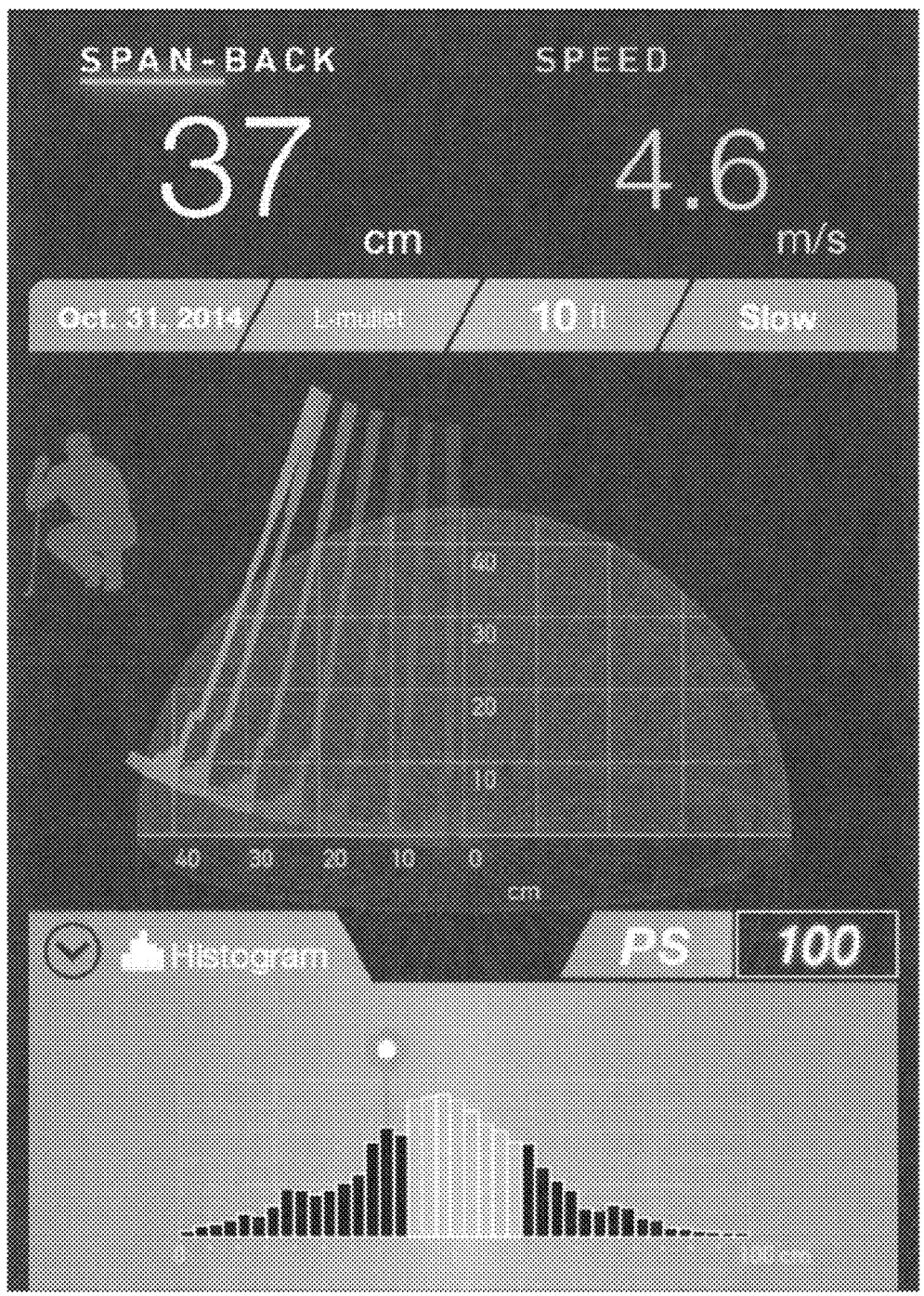
FIG. 14 is a diagram illustrating an analysis screen when "Histogram" is selected in FIG. 12 or 13.

FIGS. 12 to 16 illustrate screen examples which are subsequently displayed when "Stroke" is selected on the initial screen. FIG. 12 illustrates an example of a display screen of stroke analysis data at a single swing when "Stroke" is selected on the initial screen. FIG. 13 illustrates a screen displayed when "SPAN-BACK" is selected on the screen of FIG. 12. In FIGS. 12 and 13, 37 cm is enlarged and displayed in an emphasized manner as a stroke (SPAN-BACK) of a backswing of the putter 13 on the basis of analysis data from the stroke (swing width) analysis unit 120 illustrated in FIG. 2. If "Histogram" on the screen lower left of FIG. 12 or 13 is selected, the screen of FIG. 12 or 13 is changed to a screen of FIG. 14. A screen lower part illustrated in FIG. 14 displays a histogram indicating a distribution of strokes of the backswing on the basis of analysis data from the statistical analysis unit 140 illustrated in FIG. 2. As illustrated in FIG. 14, a position of a stroke measured this time may also be displayed in the histogram.

Figure 15:
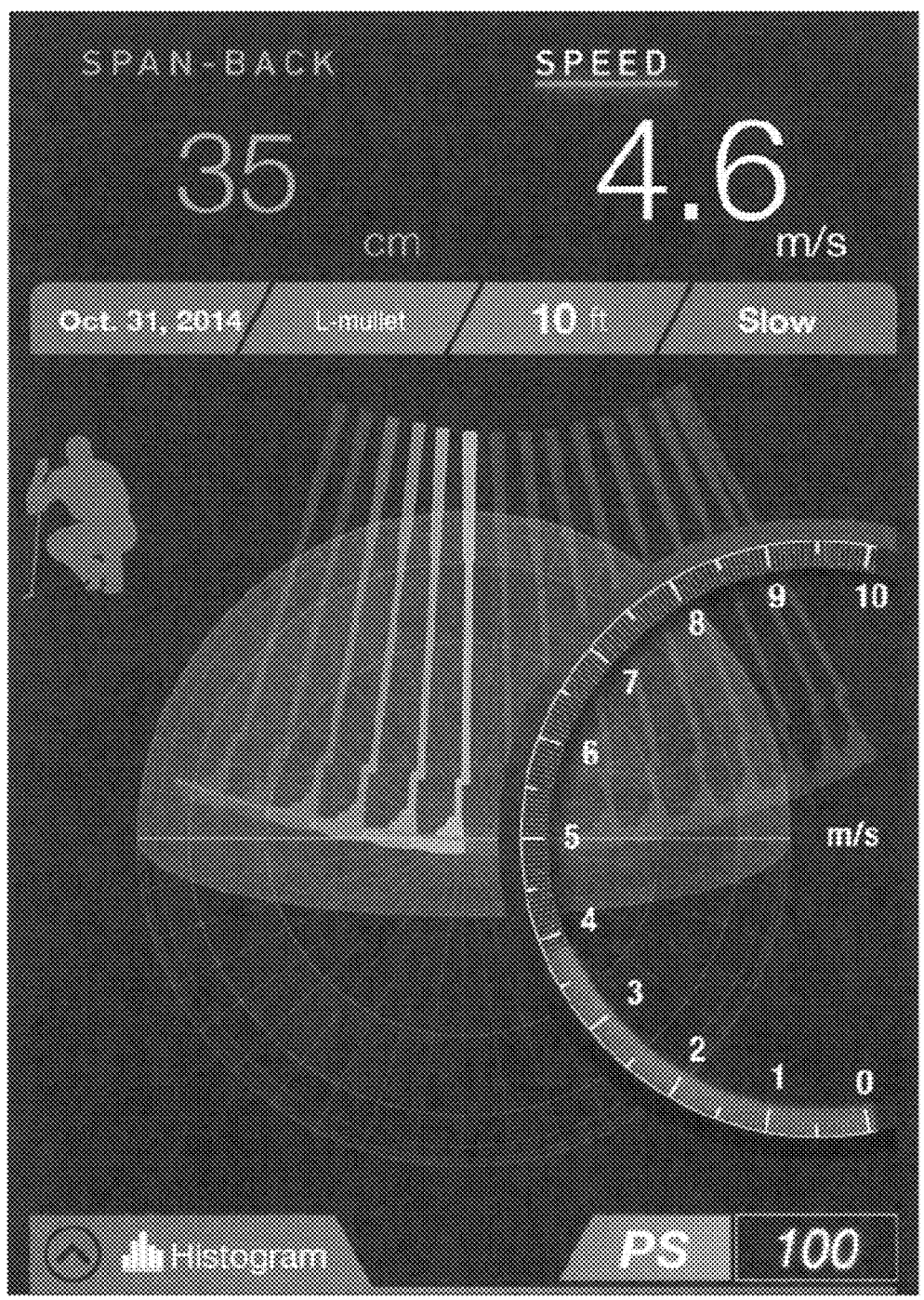
FIG. 15 is a diagram illustrating an analysis screen when "SPEED" is selected in FIGS. 12 to 14.
Figure 16:
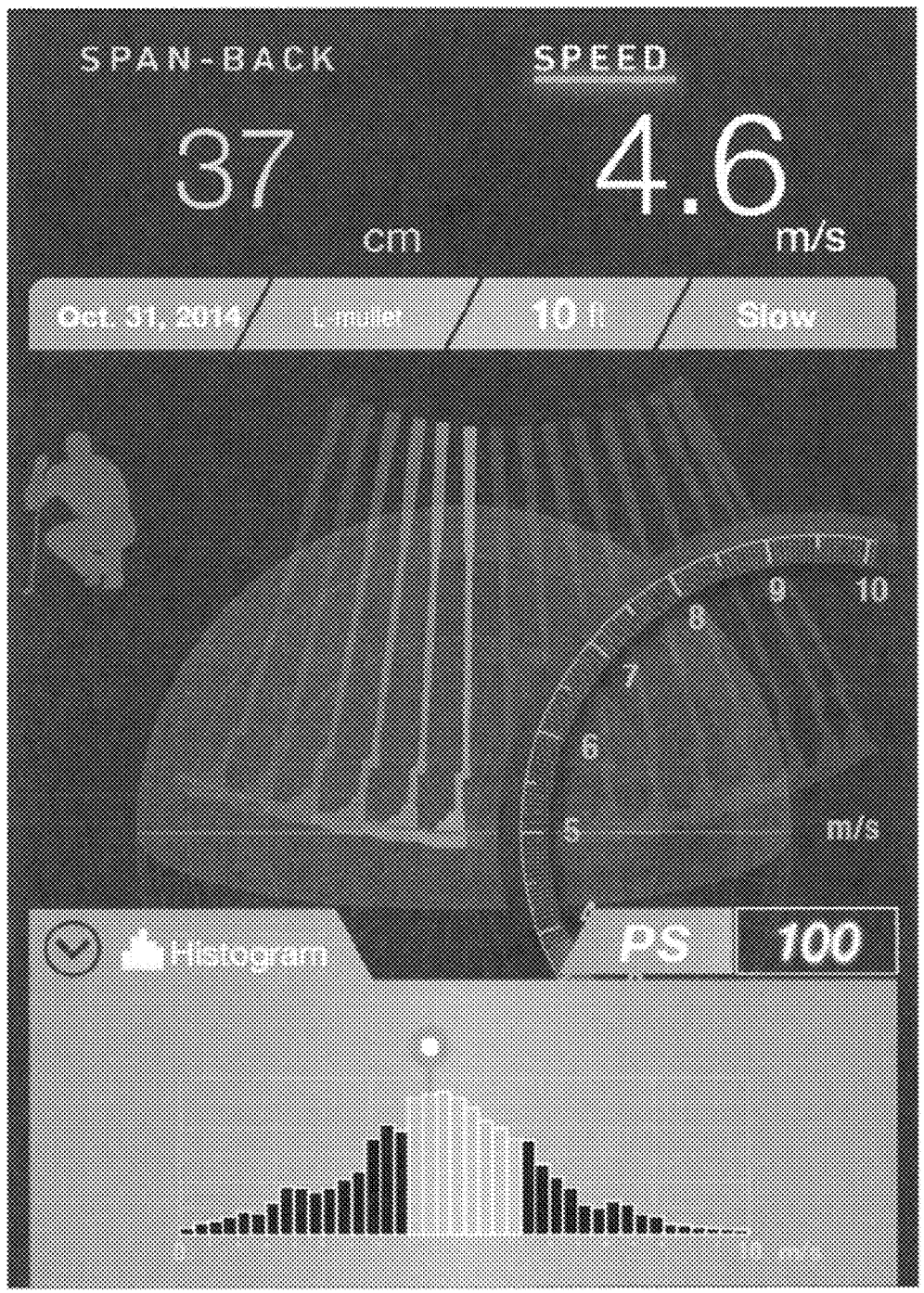
FIG. 16 is a diagram illustrating an analysis screen when "Histogram" is selected in FIG. 15.

In FIGS. 12 to 14, if "SPEED" on the screen upper right is selected, the screen is changed to a screen of FIG. 15. In FIG. 15, 4.6 m/s is enlarged and displayed in an emphasized manner as a speed of the club head 13c during impact on the basis of analysis data from the speed detection unit 60 illustrated in FIG. 2 in the column "SPEED" on the screen upper right. A speed display meter is displayed on the right side of the screen center of FIG. 15. If "Histogram" on the screen lower left of FIG. 15 is selected, the screen of FIG. 15 is changed to a screen of FIG. 16. A screen lower part illustrated in FIG. 16 displays a histogram indicating a distribution of speeds of the club head 13c during impact on the basis of analysis data from the statistical analysis unit 140 illustrated in FIG. 2. As illustrated in FIG. 16, a position of a speed measured this time may be displayed in the histogram.

(3-2-4) Rising

Figure 17:
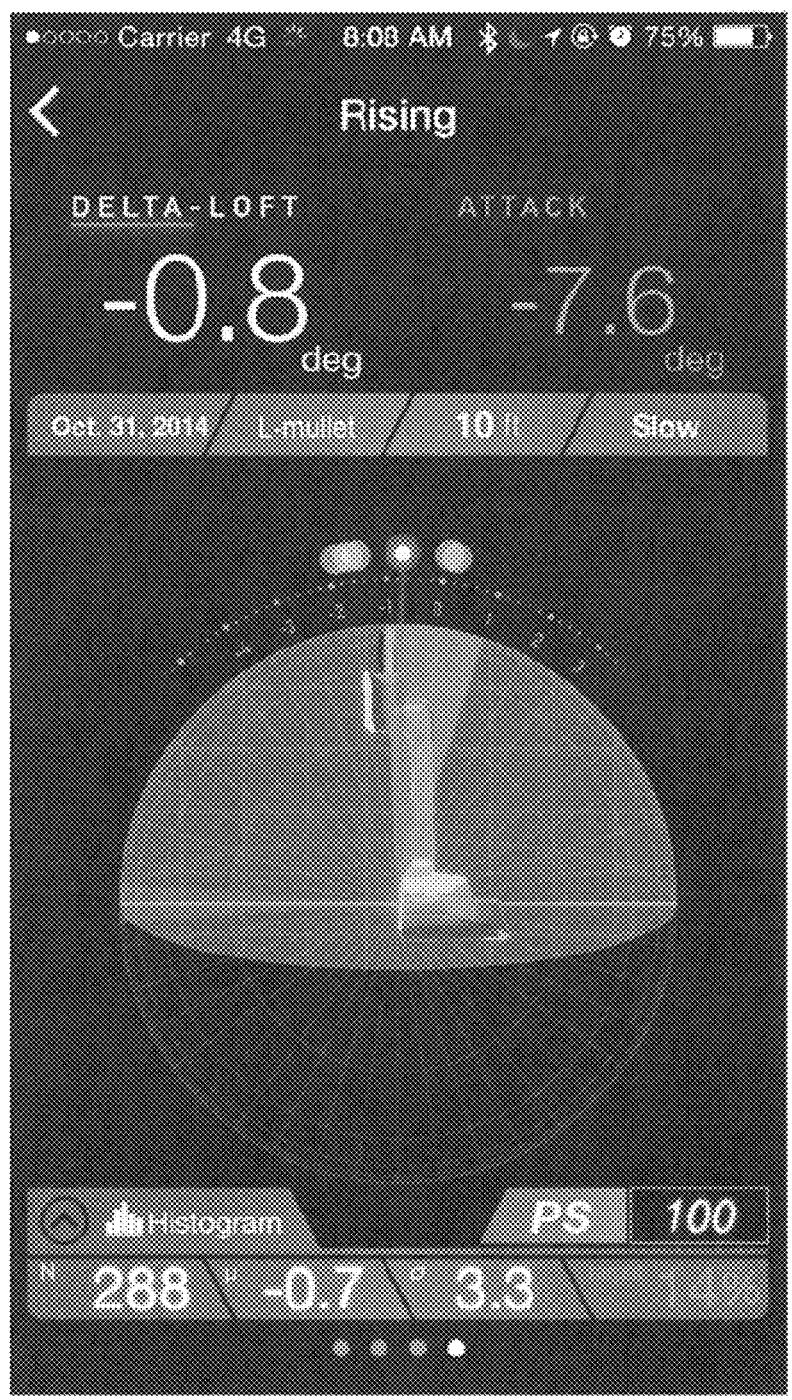
FIG. 17 is a diagram illustrating an analysis screen when "Rising" is selected in FIG. 5.
Figure 18:
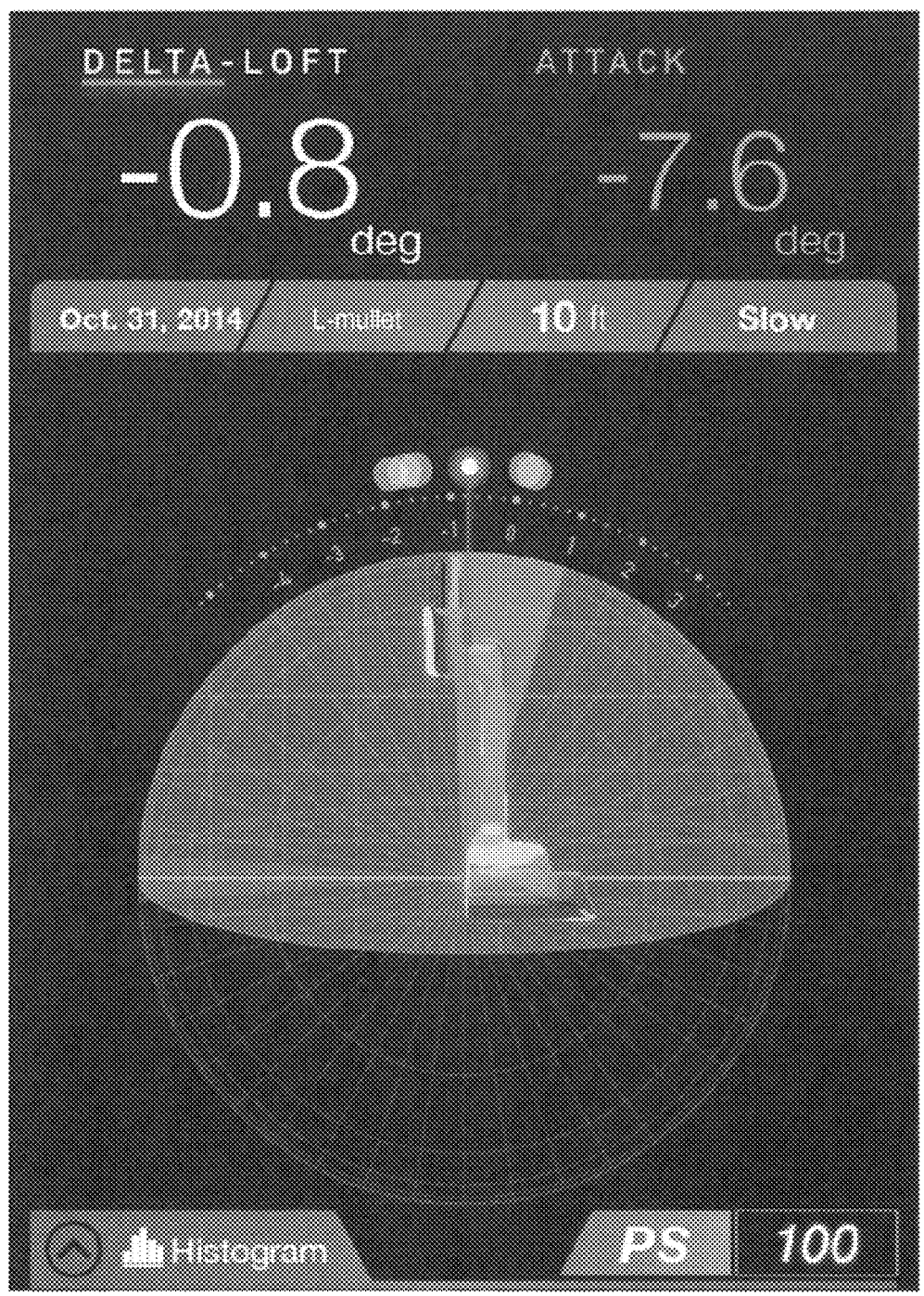
FIG. 18 is a diagram illustrating an analysis screen when "DELTA-LOFT" is selected in FIG. 17.

FIGS. 17 to 21 illustrate screen examples which are subsequently displayed when "Rising" is selected on the initial screen. FIG. 17 illustrates an example of a display screen of front-view direction analysis data at a single swing when "Rising" is selected on the initial screen. FIG. 18 illustrates a screen displayed when "DELTA-LOFT" is selected on the screen illustrated in FIG. 17. In FIGS. 17 and 18, −0.8 degrees is enlarged and displayed in an emphasized manner as the third deviation angle θ3 (delta-loft angle: DELTA-LOFT) illustrated in FIG. 4A on the basis of analysis data from the front-view direction analysis unit 110 illustrated in FIG. 2.

At the screen center of FIGS. 17 and 18, a specified inclined angle is displayed in an angle coordinate system representing a deviation angle relative to a reference inclined angle. In the angle coordinate system, 0 degrees indicates the reference inclined angle. An image indicating the club head 13c of the putter 13 in a front view of viewing a golfer (a user using an exercise appliance) from the front side is displayed. In the angle coordinate system, a specified inclined angle is displayed as an extension line of a face surface of the image. In FIGS. 17 and 18, the specified inclined angle is displayed so as to match a central line of the angle coordinate system, and a position indicating a reference angle is rotated and displayed by an intersection angle in a direction reverse to a sign of the intersection angle. The central line of the angle coordinate system may match the reference inclined angle (0 degrees), and a line indicating the specified inclined angle may be rotated and displayed in a direction coincident with a sign of the inclined angle by the inclined angle. As mentioned above, if the reference inclined angle and the inclined angle are displayed in the same coordinate system, a difference therebetween carne visually recognized.

An angle in the angle coordinate system is exaggerated larger than an actual angle, and an angle range of 1 degree is illustrated to be exaggerated several times to several tens of times. This is so that a deviation of the inclined angle relative to the reference inclined angle can be easily visually recognized.

In the angle coordinate system illustrated in FIGS. 17 and 18, a target region of, for example, ±1 degree including the reference inclined angle (0 degrees) may be displayed so as to be differentiated from other regions. In the above-described way, since a target is a zone rather than a line, a target achievement ratio is increased, the user feels comfortable, and thus an exercise practice effect can be improved.

In the angle coordinate system illustrated in FIGS. 17 and 18, inclined angles (five inclined angles in FIGS. 17 and 18) specified in the past may be displayed so as to be differentiated from an inclined angle specified this time. In the above-described manner, in a case where exercise is repeatedly performed, the achievement of a practice effect can be visually recognized.

Figure 19:
FIG. 19 is a diagram illustrating an analysis screen when "Histogram" is selected in FIG. 17 or 18.

If "Histogram" on the lower left in FIG. 17 or FIG. 18 is selected, the screen of FIG. 17 or 18 is changed to a screen of FIG. 19. A screen lower part illustrated in FIG. 19 displays a histogram indicating, for example, a distribution of inclined angles on the basis of analysis data from the statistical analysis unit 140 illustrated in FIG. 2. As illustrated in FIG. 19, a position of an inclined angle measured this time may also be displayed in the histogram.

Figure 20:
FIG. 20 is a diagram illustrating an analysis screen when "ATTACK" is selected in FIGS. 17 to 19.

In FIGS. 17 to 19, if the column "ATTACK" on the screen upper right is selected, the screen is changed to a screen of FIG. 20. In FIG. 20, −7.6 degrees is enlarged and displayed in an emphasized manner as the fourth deviation angle θ4 (attack angle) of the club head 13c during impact illustrated in FIG. 4B on the basis of analysis data from the front-view direction analysis unit 110 illustrated in FIG. 2 in the column "ATTACK" on the screen upper right. At the screen center of FIG. 20, an angle in the angle coordinate system is changed to an angle axis of the attack angle. A position of the attack angle=0 degrees in the angle coordinate system is set to a horizontal position on the screen, 0 degrees is the reference inclined angle. In FIG. 20, a normal line to a face surface of the image indicating the putter 13 in a front view of viewing the golfer (a user using an exercise appliance) from the front side is displayed at a position of the attack angle=−7.6 degrees. This normal line indicates a specified inclined angle. Also in this case, as illustrated in FIG. 20, attack angles (five attack angles in FIG. 20) specified in the past may be displayed so as to be differentiated from an attack angle specified this time.

Figure 21:
FIG. 21 is a diagram illustrating an analysis screen when "Histogram" is selected in FIG. 20.

If "Histogram" on the screen lower left of FIG. 20 is selected, the screen of FIG. 20 is changed to a screen of FIG. 21. A screen lower part illustrated in FIG. 21 displays a histogram indicating a distribution of attack angles on the basis of analysis data from the statistical analysis unit 140 illustrated in FIG. 2. As illustrated in FIG. 21, a position of an attack angle measured this time may also be displayed in the histogram.

(4) Operation of Swing Position Coordinate Detection Unit

Figure 22:
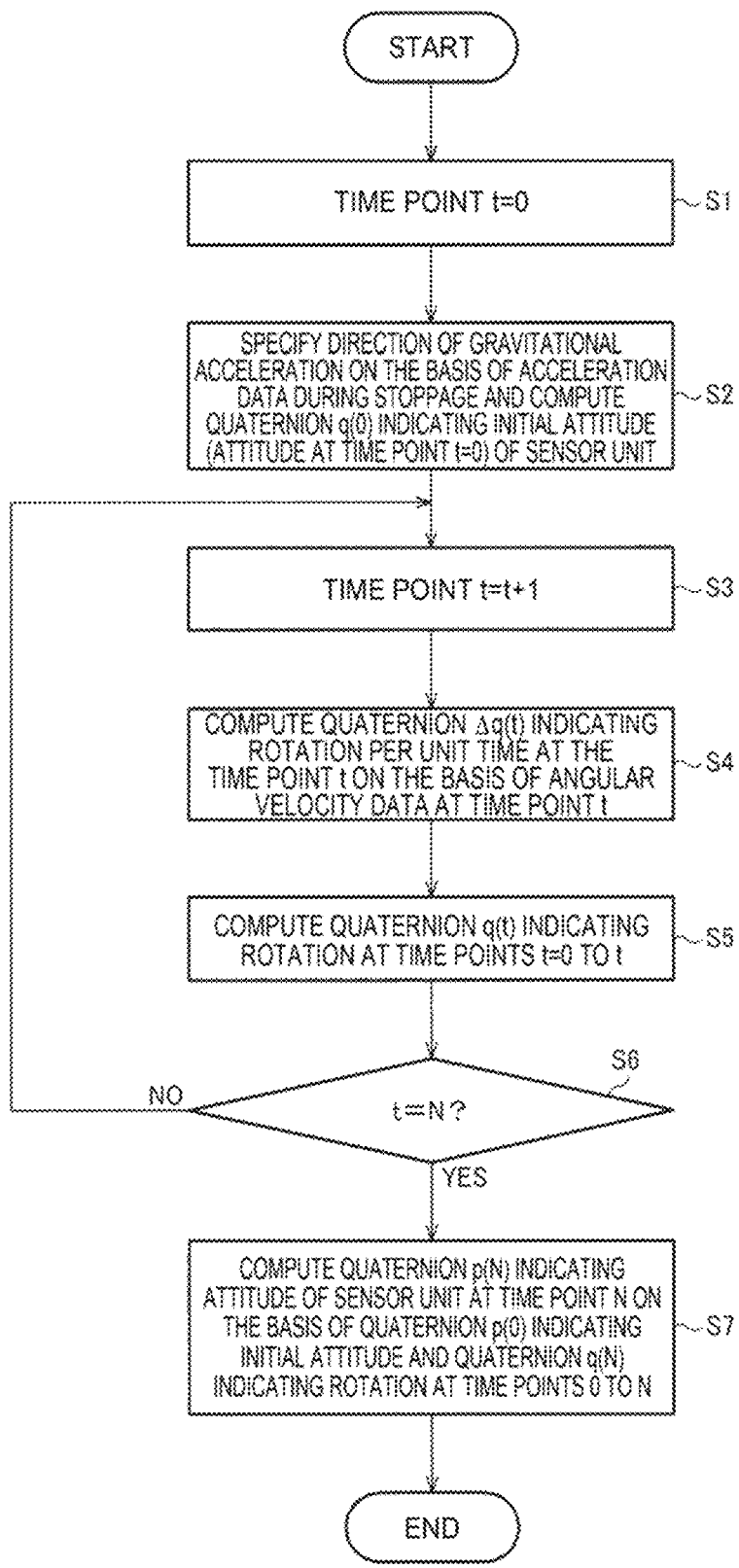
FIG. 22 is a flowchart illustrating an operation of detecting an attitude on a swing trajectory.

A description will be made of calculation performed by the swing position coordinate detection unit 50 illustrated in FIG. 2. FIG. 22 is a flowchart illustrating an example of a procedure of processes of computing attitudes (an initial attitude to an attitude at a time point N) of the sensor unit 12 in the swing position coordinate detection unit 50.

As illustrated in FIG. 22, first, the swing position coordinate detection unit 50 specifies the direction of gravitational acceleration on the basis of acceleration data in the three axes during stoppage at the time point t=0 (step S1) and computes a quaternion p(0) indicating an initial attitude (an attitude at a time point t=0) of the sensor unit (step S2).

A three-dimensional coordinate position is represented by the following Equation (1) as a quaternion q indicating rotation of a position vector.

$$q = (w, x, y, z) \quad (1)$$

In Equation (1), if a rotation angle of target rotation is θ, and unit vectors of a rotation axis are $(r_x, r_y, r_z)$, w, x, y, and z are represented by the following Equation (2).

$$w = \cos\frac{\theta}{2},\ x = r_x \cdot \sin\frac{\theta}{2},\ y = r_y \cdot \sin\frac{\theta}{2},\ z = r_z \cdot \sin\frac{\theta}{2} \quad (2)$$

Since the sensor unit 12 is stopped at the time point t=0 at the time of starting a swing (address), a quaternion q(0) indicating rotation at θ=0 and the time point t=0 is as in the following Equation (3) on the basis of Equation (1) obtained by assigning θ=0 to Equation (2).

$$q(0)=(1,0,0,0) \quad (3)$$

Next, the swing position coordinate detection unit 50 updates the time point t to t+1 (step S3). Here, the time point t=0 is updated to a time point t=1.

Next, the swing position coordinate detection unit 50 computes a quaternion Δq(t) indicating rotation per unit time at the time point t on the basis of three-axis angular velocity data at the time point t (step S4).

For example, if the three-axis angular velocity data at the time point t is ω(t)=[ω$_x$(t), ω$_y$(t), ω$_z$(t)], the magnitude |ω(t)| of angular velocity per sample measured at the time point t is computed by using the following Equation (4).

$$|\omega(t)|=\sqrt{\omega_x(t)^2+\omega_y(t)^2+\omega_w(t)^2} \quad (4)$$

The magnitude |ω(t)| of angular velocity corresponds to a rotation angle per unit time, and thus quaternion Δq(t+1) indicating rotation per unit time at the time point t is computed by using the following Equation (5).

$$\Delta q(t) = \left(\cos\frac{|\omega(t)|}{2}, \frac{\omega_x(t)}{|\omega(t)|}\sin\frac{|\omega(t)|}{2}, \frac{\omega_y(t)}{|\omega(t)|}\sin\frac{|\omega(t)|}{2}, \frac{\omega_z(t)}{|\omega(t)|}\sin\frac{|\omega(t)|}{2}\right) \quad (5)$$

Here, since t is 1, the swing position coordinate detection unit 50 computes Δq(1) by using Equation (5) on the basis of three-axis angular velocity data ω(1)=[ω$_x$(1), ω$_y$(1), ω$_z$(1)] at the time point t=1.

Next, the swing position coordinate detection unit 50 computes a quaternion q(t) indicating rotation from the time point 0 to the time point t (step S4). The quaternion q(t) is computed by using the following Equation (6).

$$q(t)=q(t-1)\cdot\Delta q(t) \quad (6)$$

Here, since t is 1, the swing position coordinate detection unit 50 computes q(1) by using Equation (6) on the basis of q(0) in Equation (3) and Δq(1) computed in step S4.

Next, the swing position coordinate detection unit 50 repeatedly performs the processes in steps S3 to S5 until t becomes N. If t becomes N (YES in step S6), the swing position coordinate detection unit 50 computes a quaternion p(N) indicating an attitude at the time point N on the basis of the quaternion p(0) indicating the initial attitude computed in step S2 and the quaternion q(N) indicating rotation from time points t=0 to N computed in the previous step S5 (step S7), and finishes the process.

The swing position coordinate detection unit 50 can obtain coordinates (X,Y,Z) in the absolute reference coordinate system of the club head 13c of the putter 13 at the time points t=0 to N on the basis of the attitude information acquired in the above-described way, and distance information from the sensor unit 12 to the club head 13c (first and second measurement points 13d and 13e which will be described later). The speed detection unit 60 illustrated in FIG. 2 can detect a speed at the coordinate position obtained by the swing position coordinate detection unit 50 on the basis of an output signal from the inertial sensor 12.

Figure 23:
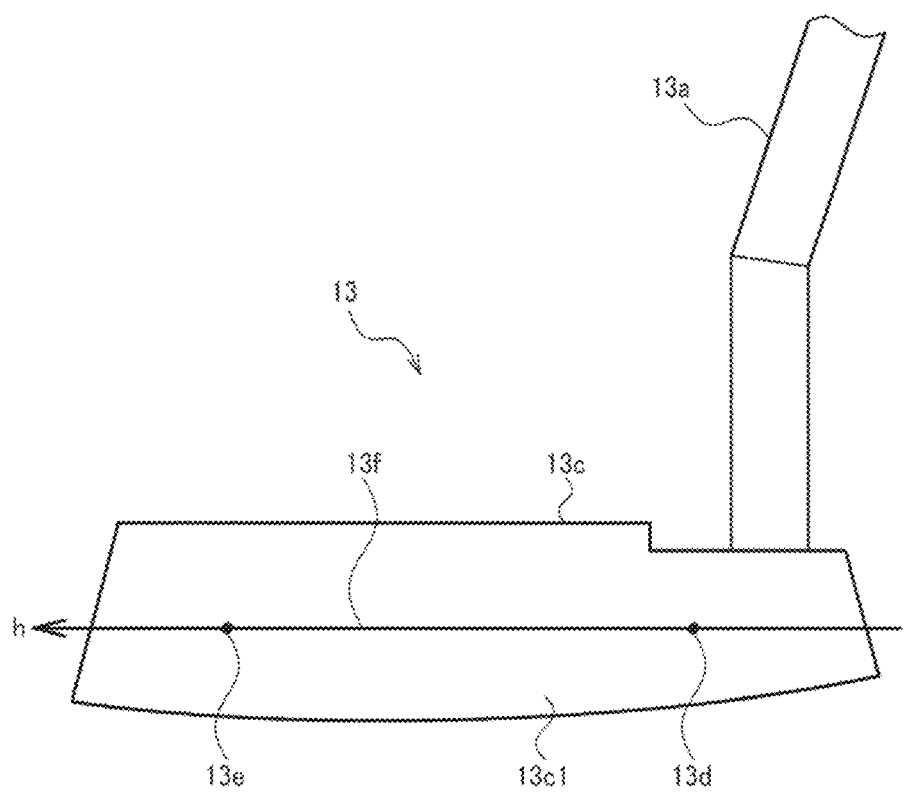
FIG. 23 is a diagram for explaining first and second measurement points which are set to be separated from each other in a horizontal direction on a face surface of a club head.
Figure 24:
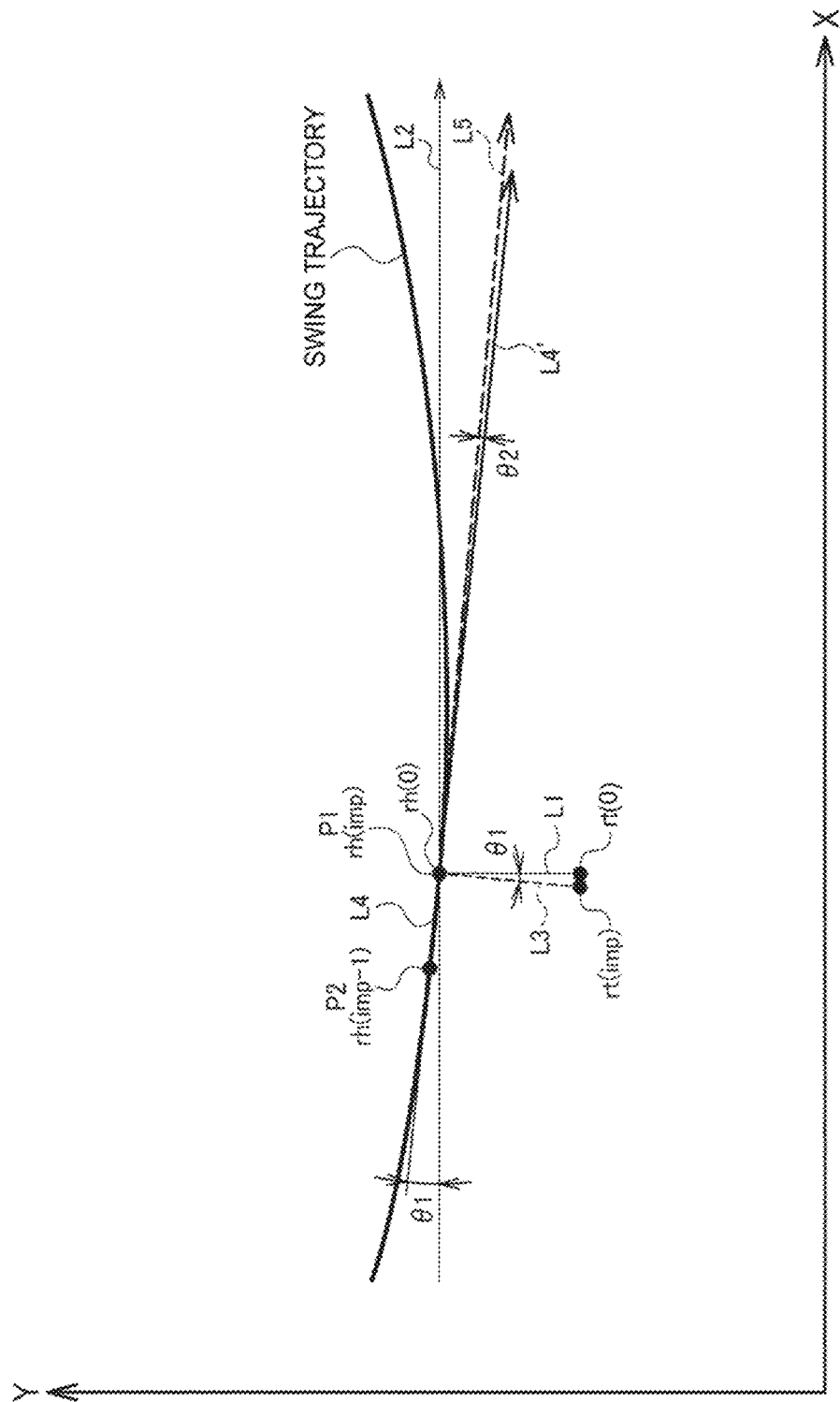
FIG. 24 is a diagram for explaining the first deviation angle (absolute face angle) and the second deviation angle (square degree).
Figure 25:
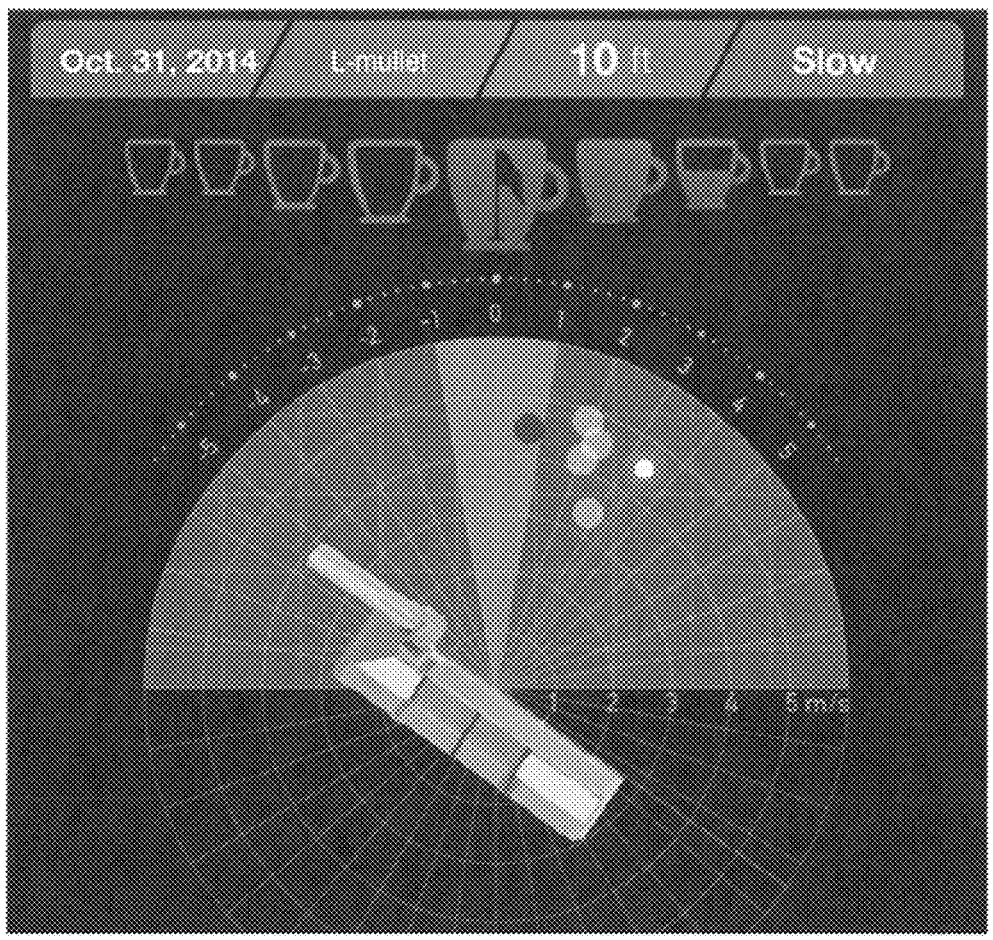
FIG. 25 is a diagram schematically illustrating a cup-in ratio in the cup unit.

(5) Analysis Units
(5-1) Analysis and Display of First Deviation Angle θ1, Second Deviation Angle θ2, and Speed V Next, with reference to FIGS. 23 to 25, a description will be made of configurations and operations of the address analysis unit 70, the impact analysis unit 80, the plan-view direction analysis unit 90, the statistical analysis unit 140, and the image processing circuit 18 related to generation of the analysis screens illustrated in FIGS. 6 to 10. First, with reference to FIG. 23, a description will be made of the first measurement point 13d and the second measurement point 13e on the face surface 13c1 of the club head 13c. As illustrated in FIG. 23, in order to specify an attitude and a position of the face surface 13c1, the first measurement point 13d and the second measurement point 13e are set on the face surface 13c1. The first measurement point 13d and the second measurement point 13e are disposed at positions separated from each other. Here, the first measurement point 13d is located on a heel side of the face surface 13c1, and the second measurement point 13e is located on a toe side of the face surface 13c1. The first measurement point 13d and the second measurement point 13e are preferably disposed on a face line h which is parallel to the ground surface and passes through a core (sweet spot) of the face surface 13c1. A line segment 13f connecting the first measurement point 13d to the second measurement point 13e can specify the direction of the face surface 13c1 when being projected onto the ground surface.

As illustrated in FIG. 2, the calculation processing circuit 14 of FIG. 1 includes the address (stoppage) analysis unit 70 and the impact analysis unit 80. The address analysis unit 70 includes an attitude specifying portion 71 and a position specifying portion 72. The attitude specifying portion 71 specifies an attitude of the face surface 13c1 in the absolute reference coordinate system ΣXYZ during stoppage (that is, during address). When an attitude is specified, for example, as illustrated in FIG. 24, the attitude specifying portion 71 connects a coordinate=r$_h$(0) of the first measurement point 13d and a coordinate=r$_t$(0) of the second measurement point 13e during stoppage to each other with a first line segment L1. An attitude of the face surface 13c1 is specified by the first line segment L1. In this case, the first line segment L1 is projected onto a horizontal plane (an X-Z plane: a surface expanding parallel to the ground) which is perpendicular to the Y axis in the absolute reference coordinate system ΣXYZ. The swing position coordinate detection unit 50 can specify positions of the first measurement point 13d and the second measurement point 13e corresponding to the address time t=0 by using the coordinate=r$_h$(0) of the first measurement point 13d and the coordinate=r$_t$(0) of the second measurement point 13e during stoppage.

The position specifying portion 72 specifies a second line segment L2 which is perpendicular to the face surface 13c1 in the absolute reference coordinate system ΣXYZ during stoppage. The second line segment L2 vertically intersects the face surface 13c1 at the first measurement point 13d=r$_h$(0). The position specifying portion 72 specifies the first line segment L1 when specifying the second line segment L2. The position specifying portion 72 sets the second line segment 12 in a vertical direction to the first line segment L1 at the first measurement point 13d. The second line segment L2 indicates a so-called target line which is a hitting target direction. In this case, the second line segment L2 is projected onto the horizontal plane which is perpendicular to the Y axis in the absolute reference coordinate system ΣXYZ in the same manner as the first line segment L1.

The impact analysis unit 80 includes, as illustrated in FIG. 2, an attitude specifying portion 81, a trajectory specifying portion 82, and a speed specifying portion 63. The attitude specifying portion 81 specifies an attitude of the face surface 13c1 in the absolute reference coordinate system ΣXYZ during impact. When the attitude is specified, for example, as illustrated in FIG. 24, the attitude specifying portion 81 connects a coordinate=r$_h$(imp) of the first measurement point 13d and a coordinate=$r_r$(imp) of the second measurement point 13e during impact to each other with a third line segment L3. An attitude of the face surface 13c1 during impact is specified by the third line segment L3. In this case, the third line segment L3 is projected onto the horizontal plane which is perpendicular to the Y axis in the absolute reference coordinate system ΣXYZ. The swing position coordinate detection unit 50 can specify positions of the first measurement point 13d and the second measurement point 13e corresponding to the impact time t=time during impact by using the coordinate $r_h$(imp) of the first measurement point 13d and the coordinate=$r_r$(imp) of the second measurement point 13e during impact. For example, considerable acceleration in a specific direction corresponding to an output signal from the inertial sensor 12 is observed at the moment of impact. The impact time t=timp is specified on the basis of a threshold value of the acceleration.

The trajectory specifying portion 82 specifies a movement trajectory of the first measurement point 13d in the absolute reference coordinate system ΣXYZ during impact. When the movement trajectory is specified, as illustrated in FIG. 24, the trajectory specifying portion 82 specifies a first coordinate point P1 on the absolute reference coordinate system ΣXYZ indicating a position $r_h$(imp) of the first measurement point 13d during impact, and a second coordinate point P2 on the absolute reference coordinate system ΣXYZ indicating a position $r_h$(imp−1) of the first measurement point 13d as a sampling point preceding the impact. Here, a sampling point right before the impact time may be allocated to the second coordinate point P2. The first coordinate point P1 and the second coordinate point P2 are connected to each other via a fourth line segment L4. The direction and the length of the fourth line segment L4 respectively indicate a direction and the magnitude of a movement vector. In this case, in the same manner as described above, the fourth line segment L4 is projected onto the horizontal plane which is perpendicular to the Y axis in the absolute reference coordinate system ΣXYZ. A direction L4' (a tangential direction during impact with respect to a movement trajectory) in which the fourth line segment L4 projected onto the horizontal plane is defined as an accurate hitting direction during impact.

The speed specifying portion 63 specifies a speed of the face surface 13c1 during impact, displayed along with the absolute face angle θ1 or the square degree θ2 in the polar coordinate system. The speed of the face surface 13c1 during impact may be obtained on the basis of information regarding acceleration or the like at an impact position.

The plan-view direction analysis unit 90 includes, as illustrated in FIG. 2, a first deviation angle analysis portion 91 and a second deviation angle analysis portion 92. The first deviation angle analysis portion 91 is connected to the position specifying portion 72 of the address analysis unit 70 and the trajectory specifying portion 82 of the impact analysis unit 80. In this case, the first deviation angle analysis portion 91 specifies, for example, the extension line L4' of the fourth line segment IA specified by the trajectory specifying portion 82 as a hitting direction. The first deviation angle analysis portion 91 calculates an intersection angle (the first deviation angle or the absolute face angle) 01 between the second line segment L2 (which is parallel to a hitting target direction or a target line) which is perpendicular to the face surface 13c1 at the first measurement point 13d on the face surface 13c1 during address, and the extension line L4' (accurate hitting direction) of the fourth line segment L4 which is perpendicular to the face surface 13c1 at the first measurement point 13d on the face surface 13c1 during impact. The first deviation angle analysis portion 91 may be connected to the position specifying portion 72 of the address analysis unit 70 and the attitude specifying portion 81 of the impact analysis unit 80. In this case, the first deviation angle analysis portion 91 temporarily sets a hitting direction L5 to a vertical direction to the third line segment L3 specified by the attitude specifying portion 81. The first deviation angle analysis portion 91 calculates an intersection angle (the first deviation angle or the absolute face angle) 01 between the second line segment L2 (which is parallel to a hitting target direction or a target line) which is perpendicular to the face surface 13c1 at the first measurement point 13d on the face surface 13c1 during address, and the hitting direction L5 which is perpendicular to the face surface 13c1 during impact.

The second deviation angle analysis portion 92 is connected to the attitude specifying portion 81 and the trajectory specifying portion 82 of the impact analysis unit 80. The second deviation angle analysis portion 92 temporarily sets the hitting direction L5 to a vertical direction to the third line segment L3 specified by the attitude specifying portion 81. In other words, as described above, the accurate hitting direction L4' is set on the extension line (a tangential direction during impact with respect to a movement trajectory) of a movement vector (the fourth line segment L4), but the face surface 13c1 in an actual attitude may not necessarily be perpendicular to the accurate hitting direction L4'. This is because the face surface 13c1 is closed or opened during impact and thus is not perpendicular to the accurate hitting direction L4'. The second deviation angle analysis portion 92 specifies the intersection angle θ2 between the accurate hitting direction L4' and the virtual hitting direction L5 as a square degree. The square degree θ2 indicates a deviation angle between a virtual vertical plane with respect to the accurate hitting direction L4' and the face surface 13c1 measured during impact.

The statistical analysis unit 140 calculates a statistical value indicating variation in the absolute face angle θ1, the square degree θ2, or the speed V during impact. The statistical analysis unit 140 includes a histogram generation portion 141. The histogram generation portion 141 sorts the absolute face angle θ1, the square degree θ2, or the speed V measured as data for the histogram illustrated in FIG. 8 or 10 into a plurality of zones, and counts the number of samples included in each zone. The statistical analysis unit 140 also includes a variation analysis portion 142. The variation analysis portion 142 calculates an average value, a standard deviation, and the like of the whole number of samples of the absolute face angle θ1, the square degree θ2, or the speedy. In the above-described way, a statistical value indicating the absolute face angle θ1, the square degree θ2, or the speed V is displayed, and thus it is possible to estimate reproducibility of the directionality and the perception of distance of a hit ball.

The image processing circuit 18 may generate display information illustrated in FIGS. 6 to 10 displayed on the display device 19 on the basis of information from the plan-view direction analysis unit 90 and the statistical analysis unit 140. In addition, the image processing circuit 18 may display the extent to which a hitting direction is deviated relative to a target region by using a multiple of the unit indicating a region corresponding to the target region on the basis of information from the plan-view direction analysis unit 90. For example, as illustrated in FIG. 25, the unit indicating a region corresponding to the target region of the golf putter 13 is a size of a cup, and, for example, it is displayed that deviation occurs by two cups, and thus it becomes easier to recognize a deviation relative to the target.

The image processing circuit 18 may display a ratio (for example, 46%) of the number of times in which a hitting direction enters a target region to the number of exercises in which the hitting direction is specified on the basis of information from the statistical analysis unit 140. In the above-described manner, a target achievement ratio can be recognized as a numerical value, and thus a notification of an exercise practice effect can be performed in a quantitative manner.

(5-2) Analysis and Display of Deviation Amount δ Relative to Sweet Spot

The hit point analysis unit 100 illustrated in FIG. 2 includes an impact angular velocity acquisition portion 101 and a deviation amount analysis portion 102. The impact angular velocity acquisition portion 101 acquires angular velocity around a long axis (the z axis of the sensor coordinate system) of the club shaft 13a during impact on the basis of an output signal from the inertial sensor 12. The deviation amount analysis portion 102 analyzes a deviation amount δ relative to the hit point illustrated in FIG. 3C on the basis of the acquired angular velocity.

Figures 26, 27:
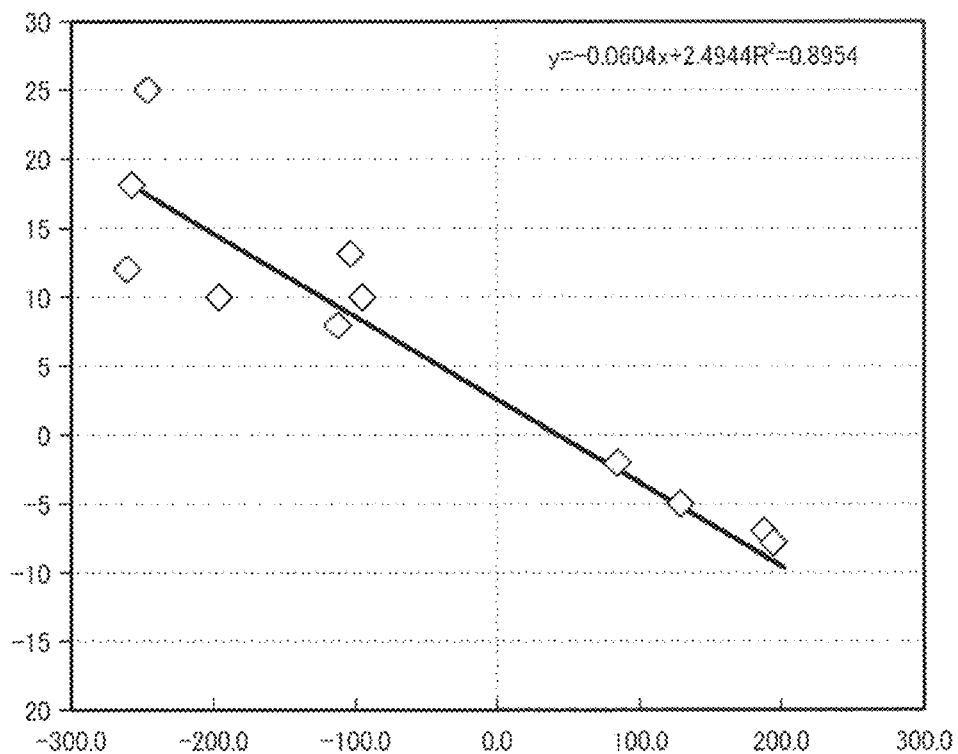
FIG. 26 is a diagram illustrating a correlation between angular velocity and a hitting point measurement value with respect to a shaft long axis.
FIG. 27 is a diagram illustrating a relational expression obtained from data illustrated in FIG. 26.

Here, FIG. 26 illustrates a relationship between angular velocity GyroZ around the long axis (the z axis of the sensor coordinate system) of the club shaft 13a, and a deviation amount δ of a hitting position relative to the sweet spot in the horizontal direction of the face surface 13c1. It can be seen from FIG. 26 that, when illustrated GyroZ is "−114.6 rad/s", a deviation amount of a hitting position relative to the sweet spot is "8 mm". FIG. 27 is a diagram illustrating the relationship illustrated in FIG. 26 as a graph. A transverse axis of the graph illustrated in FIG. 27 expresses angular velocity, and a longitudinal axis thereof expresses a deviation amount of a hitting position. The correspondence relationship in FIG. 27 may be expressed in a linear expression. A coefficient and an intercept of a linear expression may be obtained through retrogression analysis, and, in a case of the example illustrated in FIG. 27, the linear expression is represented by the following Equation (7).

$$y = -0{,}0604x + 2{.}4944 \qquad (7)$$

A contribution ratio is "$R^2 = 0.8954$".

The above Equation (7) is calculated in advance and is stored in the storage device 16. Consequently, the deviation amount analysis portion 102 can calculate the deviation amount δ of a hitting position relative to the sweet spot on the basis of information from the inertial sensor 12 and the storage device 16.

The statistical analysis unit 140 may calculate a statistical value indicating variation in the deviation amount δ. The histogram generation portion 141 sorts the measured deviation amount δ into a plurality of zones, and counts the number of samples of the deviation amount δ included in each zone in the same manner as in FIG. 8 or 10. The variation analysis portion 142 calculates an average value, a standard deviation, and the like of the whole number of samples of the deviation amount δ. In the above-described way, it is possible to display a statistical value indicating variation in the deviation amount δ.

The image processing circuit 18 may generate the display information illustrated in FIG. 11 displayed on the display device 19 on the basis of information from the hit point analysis unit 100 and the statistical analysis unit 140.

The image processing circuit 18 may display a ratio (for example, ±5 mm from the sweet spot) of the number of times in which the deviation amount δ enters a target region to the number of exercises in which the deviation amount δ is specified on the basis of information from the statistical analysis unit 140. In the above-described manner, a target achievement ratio can be recognized as a numerical value, and thus a notification of an exercise practice effect can be performed in a quantitative manner.

(5-3) Analysis and Display of Swing Width

Next, a description will be made of analysis and display of the stroke (swing width) L illustrated in FIGS. 12 to 16. The stroke (swing width) analysis unit 120 may include a position determination portion 121 and a stroke (swing width) determination portion 122 as illustrated in FIG. 2. The position determination portion 121 determines a first position which is a start point of a swing width and a second position which is an end point of the swing width on the basis of an output signal or the like from the inertial sensor 12. In the present embodiment, the first position is an address position, and thus a position corresponding to t=0 may be designated. The second position is a swing turning position, and, for example, a position where a sign of acceleration in the X axis direction (a backswing direction) of the absolute reference coordinate system is switched may be designated. The position determination portion 121 may also determine a hitting position (impact position). Considerable acceleration in a specific direction corresponding to an output signal from the inertial sensor 12 is observed at the moment of impact. The moment of impact is specified on the basis of a threshold value of the acceleration. The speed detection unit 60 may obtain a speed of the club head 13c at each position on the basis of positions from the first position to the second position, acceleration information at the impact position, and the like.

The stroke (swing width) determination portion 122 may calculate the length of a route following a swing trajectory from the first position (address position) to the second position (swing turning position) as the swing width L. Since a plurality of sampled coordinate positions from the first position to the second position are acquired, it is possible to substantially accurately calculate the length of the route by integrating a distance in a three-dimensional space between coordinate positions adjacent to each other, sampled with a fine pitch.

Figure 28:
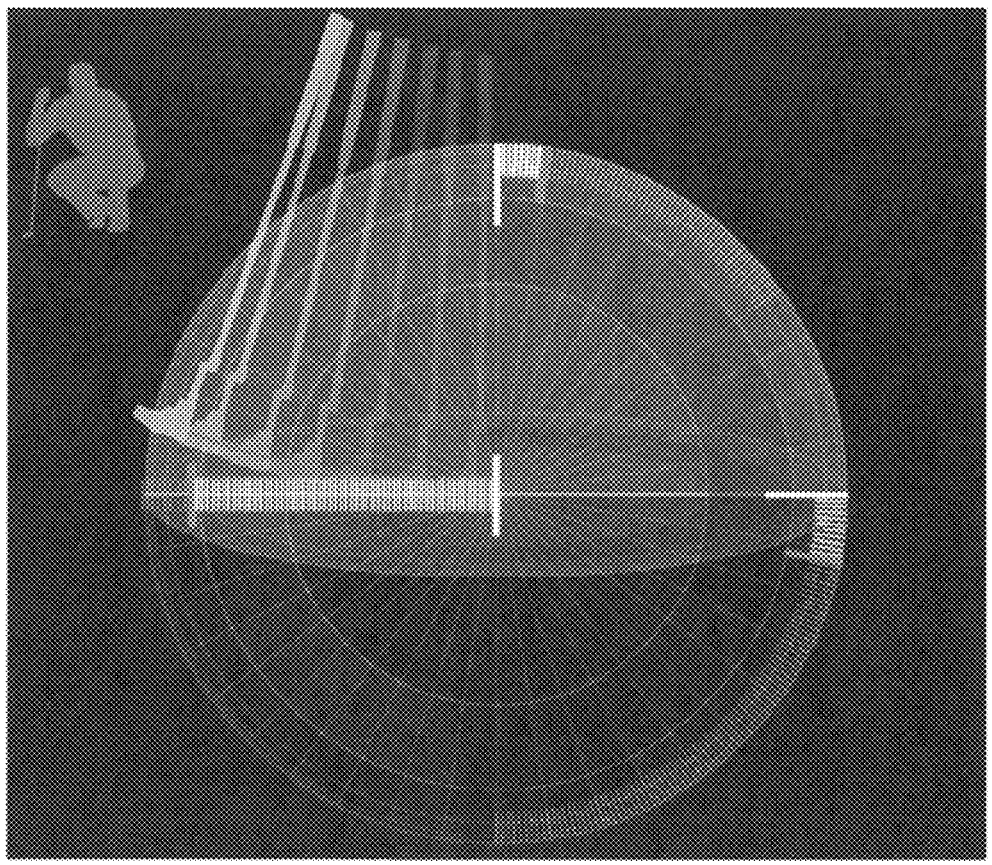
FIG. 28 is a diagram illustrating a display example in which the swing width of a backswing is projected onto a projection surface.

Alternatively, the stroke (swing width) determination portion 122 may obtain the swing width L from the first position to the second position by obtaining a distance between coordinates on a horizontal axis X of the first position and the second position projected onto a projection plane (for example, the vertical X-Y plane in the absolute reference coordinate system). This is because, for a golfer, as the swing width L during a backswing, it is sufficient to acquire a pulled length (that is, a distance between projected coordinates) in a backswing direction rather than a swing width of a more accurate route. In FIG. 28, a distance between coordinates on the horizontal axis X of the first position and the second position is expressed on a transverse axis. In FIG. 28, a distance between coordinates on a vertical axis Y of the first position and the second position, projected onto the vertical X-Y plane in the absolute reference coordinate system, is expressed on a longitudinal axis. However, a distance between coordinates on the vertical axis Y may be omitted.

The statistical analysis unit 140 may calculate a statistical value indicating variation in the swing width L. The histogram generation portion 141 sorts a swing width or a speed measured as data for the histogram illustrated in FIG. 14 or 16 into a plurality of zones, and counts the number of samples included in each zone. The variation analysis portion 142 of the statistical analysis unit 140 calculates an average value, a standard deviation, and the like of the whole number of samples of the swing width L or the speed V. In the above-described way, a statistical value indicating a variation of the swing width L or the speed V is displayed, and thus it is possible to estimate reproducibility of the swing width L or the speed v of an exercise appliance according to a traveled distance of a hit ball.

The image processing circuit 18 may generate the display information illustrated from FIGS. 17 to 21 displayed on the display device 19 on the basis of the front-view direction analysis unit 110 and the statistical analysis unit 140. In addition, the image processing circuit 18 may display a ratio (for example, 48%) of the number of times in which the third deviation angle θ3 or the fourth deviation angle θ4 enters a target region (for example, θ3=θ4=±1°) to the number of exercises in which the third deviation angle θ3 or the fourth deviation angle θ4 is specified on the basis of information from the statistical analysis unit 140. In the above-described manner, a target achievement ratio can be recognized as a numerical value, and thus a notification of an exercise practice effect can be performed in a quantitative manner.

The image processing circuit 18 may generate the display information illustrated from FIGS. 4A to 7 displayed on the display device 19 on the basis of information from the stroke (swing width) analysis unit 120 and the statistical analysis unit 140. Particularly, in FIG. 13, a display pitch of images indicating the putter 13 displayed at a plurality of positions may be made short in a period in which a swing speed obtained by the speed detection unit 60 is high, and may be made long in a period in which the swing speed is low. A single image indicating the putter 13 may be displayed for each predetermined time (every plural sampling data items). Consequently, it is possible to visually recognize both a swing width and a swing speed of the putter 13.

The image processing circuit 18 may sequentially display the images indicating the putter 13 displayed at a plurality of positions in FIG. 13 according to swing movement of the putter 13 in synchronization with the swing movement. Consequently, it is possible to visually recognize a dynamic swing width of the putter 13.

The first position which is a start point of the swing width L and the second position are not limited to setting to the above-described address position and swing turning position. As a combination of the first position and the second position, a combination of a swing turning position and an impact position for defining a swing width L of a downswing, a combination of an impact position and a swing end position for defining a swing width of follow-through, or a combination of a swing start position and a swing end position for defining a swing width L of the entire swing may be employed. Such a swing width L has a relation to a swing width of a backswing, and can contribute to gaining good reproducibility of the perception of distance, for example, in a half swing of a golf putter or iron.

(5-4) Analysis and Display of Third Deviation Angle θ3 and Fourth Deviation Angle θ4

Figure 29:
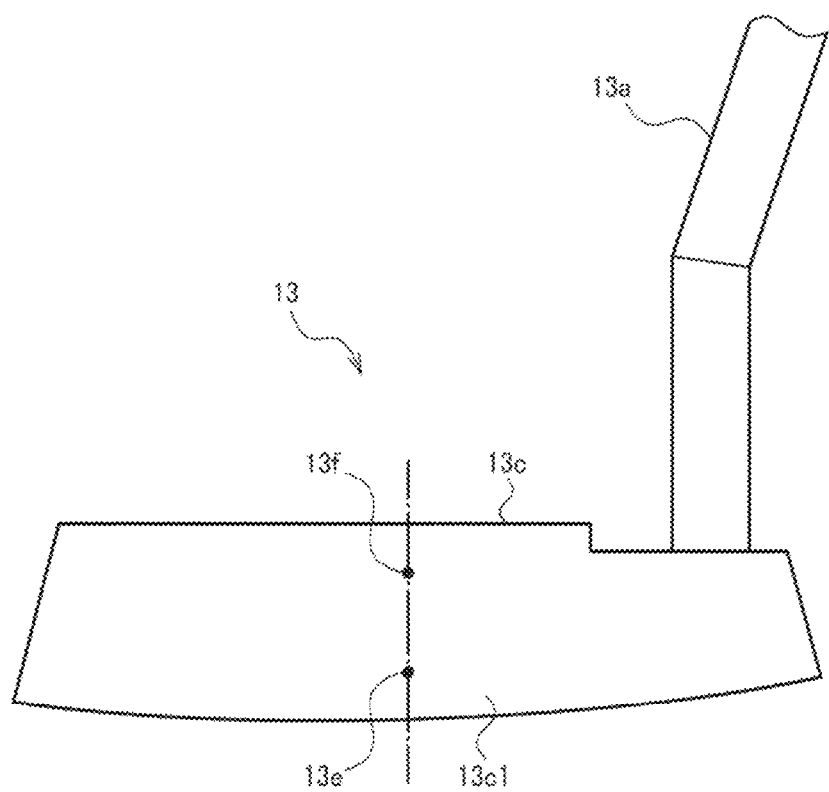
FIG. 29 is a diagram for explaining first and second measurement points which are set to be separated from each other in a vertical direction on the face surface of the club head.
Figure 30:
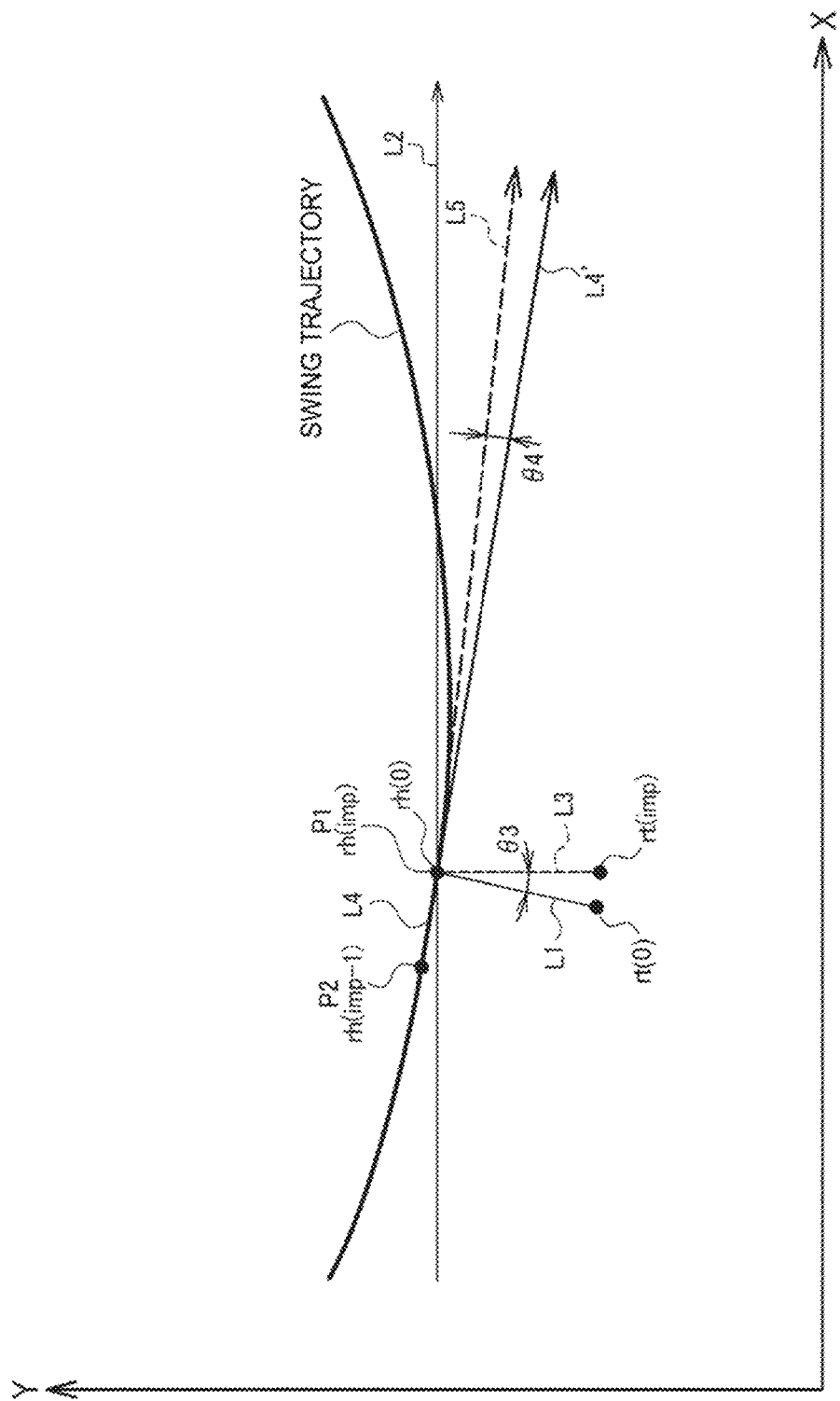
FIG. 30 is a diagram for explaining the third deviation angle (delta-loft angle) and the fourth deviation angle (attack angle).

Next, with reference to FIGS. 29 and 30, a description will be made of configurations and operations of the front-view direction analysis unit 110, the statistical analysis unit 140, and the image processing circuit 18 related to generation of the analysis screens for the third deviation angle θ3 (delta-loft angle) or the fourth deviation angle θ4 (attack angle) illustrated in FIGS. 17 to 21. First, with reference to FIG. 29, a description will be made of the first measurement point 13d and the second measurement point 13e on the face surface 13c1 of the club head 13c. As illustrated in FIG. 29, in order to specify an attitude and a position of the face surface 13c1, the first measurement point 13d and the second measurement point 13e are set on the face surface 13c1. The first measurement point 13d and the second measurement point 13e are disposed at positions separated from each other. Here, the first measurement point 13d is located on the upper side in the face surface 13c1, and the second measurement point 13e is located on a lower side in the face surface 13c1. The first measurement point 13d and the second measurement point 13e are preferably disposed on a face vertical line v which passes through a core (sweet spot) of the face surface 13c1 vertically to the ground surface. A line segment 13f connecting the first measurement point 13d to the second measurement point 13e can specify an inclined angle of the face surface 13c1 relative to the vertical surface when being projected onto the ground surface.

As illustrated in FIG. 2, the calculation processing circuit 14 includes the address (stoppage) analysis unit 70 and the impact analysis unit 80. The attitude specifying portion 71 of the address analysis unit 70 specifies an attitude of the face surface 13c1 in the absolute reference coordinate system ΣXYZ during stoppage (that is, during address). When an attitude is specified, for example, as illustrated in FIG. 30, the attitude specifying portion 71 connects a coordinate=$r_h$(0) of the first measurement point 13d and a coordinate=$r_t$(0) of the second measurement point 13e during stoppage to each other with a first line segment L1. An attitude of the face surface 13c1 is specified by the first line segment L1. In this case, the first line segment L1 is projected onto a vertical plane (an X-Y plane: a surface perpendicular to the ground) which is perpendicular to the Z axis in the absolute reference coordinate system ΣXYZ. The swing position coordinate detection unit 50 can specify positions of the first measurement point 13d and the second measurement point 13e corresponding to the address time t=0 by using the coordinate=$r_h$(0) of the first measurement point 13d and the coordinate=$r_t$(0) of the second measurement point 13e during stoppage.

The position specifying portion 72 specifies a second line segment L2 which is perpendicular to the face surface 13c1 in the absolute reference coordinate system ΣXYZ during stoppage. The second line segment L2 vertically intersects the face surface 13c1 at the first measurement point 13d=$r_h$(0). The position specifying portion 72 specifies the first line segment L1 when specifying the second line segment L2. The position specifying portion 72 sets the second line segment L2 in a vertical direction to the first line segment L1 at the first measurement point 13d. The second line segment L2 indicates a so-called target line which is a hitting target direction. In this case, the second line segment L2 is projected onto the vertical plane which is perpendicular to the Z axis in the absolute reference coordinate system ΣXYZ in the same manner as the first line segment L1.

The attitude specifying portion 81 of the impact analysis unit 80 specifies an attitude of the face surface 13c1 in the absolute reference coordinate system ΣXYZ during impact. When the attitude is specified, for example, as illustrated in FIG. 30, the attitude specifying portion 81 connects a coordinate=$r_h$(imp) of the first measurement point 13d and a coordinate=$r_t$(imp) of the second measurement point 13e during impact to each other with a third line segment L3. An attitude of the face surface 13c1 during impact is specified by the third line segment L3. In this case, the third line segment L3 is projected onto the vertical plane which is perpendicular to the Z axis in the absolute reference coordinate system ΣXYZ. The swing position coordinate detection unit 50 can specify positions of the first measurement point 13d and the second measurement point 13e corresponding to the impact time t=timp during impact by using the coordinate=$r_h$(imp) of the first measurement point 13d and the coordinate=$r_t$(imp) of the second measurement point 13e during impact. For example, considerable acceleration in a specific direction corresponding to an output signal from the inertial sensor 12 is observed at the moment of impact. The impact time t=timp is specified on the basis of a threshold value of the acceleration.

The trajectory specifying portion 82 specifies a movement trajectory of the first measurement point 13d in the absolute reference coordinate system ΣXYZ during impact. When the movement trajectory is specified, as illustrated in FIG. 30, the trajectory specifying portion 82 specifies a first coordinate point P1 on the absolute reference coordinate system ΣXYZ indicating a position $r_h$(imp) of the first measurement point 13d during impact, and a second coordinate point P2 on the absolute reference coordinate system ΣXYZ indicating a position $r_h$(imp−1) of the first measurement point 13d as a sampling point preceding the impact. Here, a sampling point right before the impact time may be allocated to the second coordinate point P2. The first coordinate point P1 and the second coordinate point P2 are connected to each other via a fourth line segment L4. A direction and the length of the fourth line segment L4 respectively indicate a direction and the magnitude of a movement vector. In this case, in the same manner as described above, the fourth line segment L4 is projected onto the vertical plane which is perpendicular to the Z axis in the absolute reference coordinate system ΣXYZ. A direction L4' (a tangential direction during impact with respect to a movement trajectory projected onto the vertical plane) in which the fourth line segment L4 projected onto the vertical plane is defined as a hitting direction during impact.

The front-view direction analysis unit 110 includes, as illustrated in FIG. 9, a third deviation angle analysis portion 111 and a fourth deviation angle analysis portion 112. The third deviation angle analysis portion 111 is connected to the position specifying portion 72 of the address analysis unit 70 and the attitude specifying portion 81 of the impact analysis unit 80. In this case, the third deviation angle analysis portion 111 specifies an intersection angle between the first line segment L1 (a line segment indicating a reference inclined angle) specified by the position specifying portion 72 and the third line segment L3 (a line segment indicating an inclined angle) specified by the attitude specifying portion 81, as the third deviation angle θ3 (delta-loft angle).

The fourth deviation angle analysis portion 112 is connected to the attitude specifying portion 71 of the address analysis unit 70 and the trajectory specifying portion 82 of the impact analysis unit 80. The fourth deviation angle analysis portion 112 specifies, for example, the extension line L4' of the fourth line segment L4 specified by the trajectory specifying portion 82 as a hitting direction. The fourth deviation angle analysis portion 112 calculates an intersection angle between the second line segment L2 (which is parallel to a hitting target direction or a target line) which is perpendicular to the face surface 13c1 at the first measurement point 13d on the face surface 13c1 during address, and the extension line L4' (accurate hitting direction) of the fourth line segment L4 which is perpendicular to the face surface 13c1 at the first measurement point 13d on the face surface 13c1 during impact, as the fourth deviation angle θ4 (attack angle).

The statistical analysis unit 140 calculates a statistical value indicating variation in the third deviation angle θ3 or the fourth deviation angle θ4. The statistical analysis unit 140 sorts the third deviation angle θ3 or the fourth deviation angle θ4 measured as data for the histogram illustrated in FIG. 19 or FIG. 21 into a plurality of zones, and counts the number of samples included in each zone. In addition, the statistical analysis unit 140 may calculate an average value, a standard deviation, and the like of the whole number of samples of the third deviation angle θ3 or the fourth deviation angle θ4. In the above-described way, a statistical value indicating variation in the third deviation angle θ3 or the fourth deviation angle θ4 is displayed, and thus it is possible to estimate reproducibility of the directionality and the perception of distance of a hit ball.

The image processing circuit 18 may generate the display information illustrated from FIGS. 17 to 21 displayed on the display device 19 on the basis of information from the front-view direction analysis unit 110 and the statistical analysis unit 140. In addition, the image processing circuit 18 may display a ratio (for example, 48%) of the number of times in which the third deviation angle θ3 or the fourth deviation angle θ4 enters a target region (for example, θ3=θ4=±1°) to the number of exercises in which the third deviation angle θ3 or the fourth deviation angle θ4 is specified on the basis of information from the statistical analysis unit 140. In the above-described manner, a target achievement ratio can be recognized as a numerical value, and thus a notification of an exercise practice effect can be performed in a quantitative manner.

(6) Scoring

Next, a description will be made of the score analysis unit 130 which scores swings on the basis of the above-described plurality of analysis data items. The scoring is roughly classified into scoring of analysis items (the first to fourth deviation angles θ1 to θ4, the swing width L, the deviation amount δ relative to a sweet spot, and the speed V during impact) and scoring of the total point obtained by weighting a plurality of analysis items.

(6-1) Scoring of Each Analysis Item

The performance score (PS) is represented by the following equation.

$$PS=P-(1-Ta)\times S \quad (8)$$

Here, P indicates a perfect score (100 points), and Ta indicates target zone estimation and is represented by the following equation.

$$Ta=(Tz-(|T-R|))/Tz \quad (9)$$

Here, Tz indicates a target zone, T indicates a target value, and R indicates analysis data. If (1−Ta) is 0 to 1, this indicates that convergence to the target zone occurs. It is indicated that (1−Ta) coming closer to 0 approaches the target value. If (1−Ta) is equal to or greater than 1, this indicates a deviation relative to the target zone. In addition, S indicates a scale number and is used for scale matching between a point and a data numerical value. S is represented by P/A, and, here, A indicates an analysis possible range.

(6-1-1) Performance Score PsF of First Deviation Angle θ1

If a square impact is applied toward a target line, the first deviation angle θ1 is 0, and, in this case, 100 points are given as PsF. A score of the first deviation angle θ1 is computed by assigning, for example, P=100, T=0, Tz=1°, A=30, and R=θ1 to Equations (8) and (9). In this case, the target zone Tz is a variable value which may be set to ±arcsin (R/L) by using the radius R of the cup and a distance L from the address position to the cup center as described above.

(6-1-2) Performance Score PsS of Second Deviation Angle $\theta_2$

If a square impact is applied on a club path, the second deviation angle $\theta_2$ is 0, and, in this case, 100 points are given as PsS. A score of the second deviation angle $\theta_2$ is computed by assigning, for example, P=100, T=0, Tz=1°, A=30, and R=$\theta_2$ to Equations (8) and (9).

(6-1-3) Performance Score PsH of Deviation Amount $\delta$ Relative to Sweet Spot If hitting is performed at the sweet spot, the as deviation amount $\delta$ is 0, and, in this case, 100 points are given as PsH. A score of the deviation amount $\delta$ is computed by assigning, for example, P=100, T=0, Tz=5°, A=100, and R=6 to Equations (8) and (9).

(6-1-4) Performance Score PsB of Swing Width L

It is targeted that the swing width L is put in a standard deviation of 1$\sigma$. A score of the swing width L is computed by assigning, for example, P=100, T=0, Tz=1e, A=100, and R=L to Equations (8) and (9).

(6-1-5) Performance Score PsI of Impact Speed V

It is targeted that the impact speed V is also put in a standard deviation of 1$\sigma$. A score of the impact speed V is computed by assigning, for example, P=100, T=0, Tz=1$\sigma$, A=10, and R=V to Equations (8) and (9).

(6-1-6) Performance Score PsL of Third Deviation Angle $\theta_3$

If an impact is applied according to a standard loft angle or an actually measured loft angle during address, the third deviation angle $\theta_3$ is 0, and, in this case, 100 points are given as PsL. A score of the third deviation angle $\theta_3$ is computed by assigning, for example, P=100, T=0, Tz=1°, A=15, and R=$\theta_3$ to Equations (8) and (9).

(6-1-7) Performance Score PsA of Fourth Deviation Angle $\theta_4$

If an impact which is parallel to a target line is applied, the fourth deviation angle $\theta_4$ is 0, and, in this case, 100 points are given as PsA. A score of the fourth deviation angle $\theta_4$ is computed by assigning, for example, P=100, T=0, Tz=1°, A=15, and R=$\theta_4$ to Equations (8) and (9).

The performance score PS of each analysis item is displayed as a numerical value in the PS column of the above-described analysis screen of the analysis item.

(6-2) Scoring of Total Point

The above-described analysis items are roughly classified into the analysis items (the first deviation angle $\theta_1$, the second deviation angle $\theta_2$, and the deviation amount $\delta$ relative to the sweet spot) regarding the directionality and the analysis items (the impact speed V, the swing width L, the third deviation angle $\theta_3$, and the fourth deviation angle $\theta_4$) regarding the perception of distance. Therefore, as total points obtained by weighting the analysis items, three types of total points are useful, including 1) a total point regarding the directionality, 2) a total point regarding the perception of distance, and 3) a total point regarding the directionality and the perception of distance.

(6-2-1) Scoring of Total Point of Analysis Item Regarding Directionality of Hit Ball Weighting factors when the three analysis items (the first deviation angle $\theta_1$, the second deviation angle $\theta_2$, and the deviation amount $\delta$ relative to the sweet spot) regarding the directionality are defined as follows. A weighting factor of the performance score PsS regarding the first deviation angle $\theta_1$ (absolute face angle) is set to WS, a weighting factor of the performance score PsF regarding the second deviation angle $\theta_2$ (square degree) is set to WF, and a weighting factor of the performance score PsH regarding the deviation amount $\delta$ relative to the sweet spot is set to WH.

When the extent of the influence on the directionality of a hit ball is taken into consideration, the weighting factor WS for the first deviation angle $\theta_1$ is higher than the weighting factor WH for the deviation amount $\delta$ (WS>WH). The weighting factor WH for the deviation amount $\delta$ is higher than the weighting factor WF for the second deviation angle $\theta_2$ (WH>WF). Therefore, the three weighting factors have the following relationship.

$$WS > WH > WF \tag{10}$$

A total point of the analysis items regarding the directionality of a hit ball is as follows in a case of using the three data items $\theta_1$, $\theta_2$, and $\delta$.

$$\text{SUM (respective } PSs \times \text{weighting factors)/SUM (respective weighting factors)} = (PsF \times WF + PsS \times WS + PsH \times WH)/(WF + WS + WH) \tag{11}$$

A total point of the analysis items regarding the directionality of a hit ball is as follows in a case of using the two data items $\theta_1$ and $\delta$.

$$\text{SUM (respective } PSs \times \text{weighting factors)/SUM (respective weighting factors)} = (PsF \times WF + PsH \times WH)/(WF + WH) \tag{12}$$

A total point of the analysis items regarding the directionality of a hit ball is as follows in a case of using the two data items $\theta_2$ and $\delta$, $$\text{SUM (respective } PSs \times \text{weighting factors)/SUM (respective weighting factors)} = (PsS \times WS + PsH \times WH)/(WS + WH) \tag{13}$$

A total point of the analysis items regarding the directionality of a hit ball is as follows in a case of using the two data items $\theta_1$ and $\theta_2$, $$\text{SUM (respective } PSs \times \text{weighting factors)/SUM (respective weighting factors)} = (PsF \times WF + PsS \times WS)/(WF + WS) \tag{14}$$

(6-2-2) Scoring of Total Point of Analysis Item Regarding Perception of Distance of Hit Ball Weighting factors when the four analysis items (the impact speed V, the swing width L, the third deviation angle $\theta_3$, and the fourth deviation angle $\theta_4$) regarding the perception of distance are defined as follows. A weighting factor of the performance score PsI regarding the impact speed V is set to WI, a weighting factor of the performance score PsB regarding the swing width L is set to WB, a weighting factor of the performance score PsL regarding the third deviation angle $\theta_3$ (delta-loft angle) is set to WL, and a weighting factor of the performance score PsA regarding the fourth deviation angle $\theta_4$ (attack angle) is set to WA.

When the extent of the influence on the perception of distance of a hit ball is taken into consideration, the weighting factor WI for the impact speed V is higher than the weighting factor WB for the swing width L (WI>WB). The weighting factor WB for the swing width L is higher than the weighting factor WL for the third deviation angle $\theta_3$ and the weighting factor WA for the fourth deviation angle $\theta_4$ (WI>WB>WL, and WI>WB>WA). The weighting factor WL for the third deviation angle $\theta_3$ and the weighting factor WA for the fourth deviation angle $\theta_4$ may set to be equal to each other since the weighting factor WL for the third deviation angle $\theta_3$ and the weighting factor WA for the fourth deviation angle $\theta_4$ have a correlation to each other (WL=WA). Therefore, the four weighting factors have the following relationship.

$$WI > WB > WL = WA \tag{15}$$

A total point of the analysis items regarding the perception of distance of a hit ball is as follows in a case of using the four data items V, L, θ3, and θ4.

SUM (respective $PSs$×weighting factors)/SUM (respective weighting factors)=($PsI$×$WI$+$PsB$×$WB$+$PsL$×$WL$+$PsA$×$WA$)/($WI$+$WB$+$WL$+$WA$) (16)

A total point of the analysis items regarding the perception of distance of a hit ball is as follows in a case of using the three data items V, L, and θ3.

SUM (respective $PSs$×weighting factors)/SUM (respective weighting factors)=($PsI$×$WI$+$PsB$×$WB$+$PsL$×$WL$)/($WI$+$WB$+$WL$) (17)

A total point of the analysis items regarding the perception of distance of a hit ball is as follows in a case of using the three data items V, L, and θ4.

SUM (respective $PSs$×weighting factors)/SUM (respective weighting factors)=($PsI$×$WI$+$PsB$×$WB$+$PsA$×$WA$)/($WI$+$WB$+$WA$) (18)

A total point of the analysis items regarding the perception of distance of a hit ball is as follows in a case of using the two data items V and L.

SUM (respective $PSs$×weighting factors)/SUM (respective weighting factors)=($PsI$×$WI$+$PsB$×$WB$)/($WI$+$WB$) (19)

(6-2-3) Scoring of Total Point of Analysis Item Regarding Directionality and Perception of Distance of Hit Ball Of the directionality and the perception of distance of a hit ball, the directionality of a hit ball is emphasized when taking into consideration the extent of the influence on swing improvement or sports. An analysis item (for example, V or L) which has a great influence among the analysis items regarding the perception of distance of a hit ball may be emphasized more than an analysis item (for example, θ2) which has a small influence among the analysis items regarding the directionality of a hit ball. Therefore, the weighting factors for the seven analysis items (θ1, θ2, δ, V, L, θ3, and θ4) regarding the directionality and the perception of distance of a hit ball have the following relationship on the basis of Equations (10) and (15).

$WS$>$WH$>$WI$>$WB$>$WF$>$WL$=$WB$ (20)

A comprehensive performance score Ps (directionality+ perception of distance) of the performance score Ps (directionality) regarding the directionality represented by any one of Equations (11) to (14) and the performance score Ps (perception of distance) regarding the directionality represented by any one of Equations (16) to (18) is as follows.

Performance score $Ps$(directionality+perception of distance)=$a$×performance score $Ps$(directionality)+$b$×performance score $Ps$(perception of distance) (21)

Here, the weighting factors a and b may be a=b=1, and, in other cases, may be a>b so that the directionality is emphasized.

The performance score Ps (directionality+perception of distance) and a×performance score Ps (directionality) or b×performance score Ps (perception of distance) may be displayed as scores, and analysis data of the plurality of analysis items used for the displayed performance scores may also be displayed with, for example, a radar chart.

Although the present embodiment has been described in detail, it is easily understood by a person skilled in the art that various modifications may occur without substantially departing from the novel matters and effects of the invention. Therefore, such modification examples are all intended to be included in the scope of the invention. For example, in the specification or the drawings, a terminology which is described at least once along with another terminology which has a broader meaning or the same meaning may be replaced with another terminology in any location of the specification or the drawings. In addition, configurations and operations of the inertial sensor 12, the golf club 13, the calculation processing circuit 14, and the like are not limited to those described in the present embodiment and may be variously modified. For example, the invention is not limited to golf, and is applicable to exercise appliances of baseball or tennis.

The entire disclosure of Japanese Patent Application No. 2015-025693, filed Feb. 12, 2015 is expressly incorporated by reference herein.

What is claimed is:

1. A motion analysis method for allowing a user to gain accuracy of reproducing a swing width of a putter corresponding to a traveled distance of a hit hall, the method comprising:
    providing an inertial sensor comprising an acceleration sensor and a gyro sensor, the inertial sensor attached to a shaft of the putter having a hitting surface angled in relation to a longitudinal axis of the putter, wherein the inertial sensor is configured to communicate wirelessly with a swing analyzing device;
    swinging the putter along a swing trajectory from a first position to a second position, the swing trajectory having a magnitude corresponding to a putting swing;
    wirelessly receiving an output signal from the inertial sensor on the swing analyzing device;
    using a processor on the swing analyzing device to determine the swing width of the swing trajectory from the first position to the second position on the basis of (i) a swing position of the putter which is acquired by using the output signal from the inertial sensor, and (ii) a distance from the inertial sensor to a predetermined location along the putter;
    displaying on the swing analyzing device the swing width for each swing motion of the putter.

2. The motion analysis method according to claim 1, wherein the first position is a swing start position, and the second position is a swing turning position.

3. The motion analysis method according to claim 1, wherein the first position is a swing turning position, and the second position is a hitting position.

4. The motion analysis method according to claim 1, wherein the first position is a hitting position, and the second position is a swing end position.

5. The motion analysis method according to claim 1, wherein the first position is a swing turning position, and the second position is a swing end position.

6. The motion analysis method according to claim 1, wherein the first position is a stoppage position when the swing is started, and the second position is a swing end position.

7. The motion analysis method according to claim 2, wherein the swing width is a length of the swing trajectory from the first position to the second position.

8. The motion analysis method according to claim 2, wherein the swing width is a length obtained by projecting the swing trajectory from the first position to the second position onto a projection plane.

9. The motion analysis method according to claim 2, wherein images indicating the putter are displayed at a plurality of positions on the swing trajectory of the putter from the first position to the second position.

10. The motion analysis method according to claim 9, wherein a display pitch of the images displayed at the plurality of positions is at a first pitch in a period in which a swing speed is at a first speed, and is at a second pitch, longer than the first pitch, in a period in which the swing speed is at a second speed, lower than the first speed.

11. The motion analysis method according to claim 10, wherein the images displayed at the plurality of positions are sequentially displayed in synchronization with swing movement according to the swing movement of the putter.

12. The motion analysis method according to claim 2, wherein variation in the swing width is displayed.

13. A motion analysis system for allowing a user to gain accuracy of reproducing a swing width of a putter corresponding to a traveled distance of a hit ball, the system comprising:
a swing analyzing device configured with a processor and memory;
the putter having a shaft;
an inertial sensor comprising an acceleration sensor and a gyro sensor and configured to communicate wirelessly with the swing analyzing device, the inertial sensor mounted to the shaft; and
wherein the swing analyzing device is configured to use the processor to determine: the swing width from a first position to a second position on a swing trajectory, having a magnitude corresponding to a putting swing, on the basis of: (i) a swing position of the putter which is acquired by using an output signal from the inertial sensor, and (ii) a distance from the inertial sensor to a predetermined location along the putter;
displaying the swing width for each swing motion of the putter.

14. The motion analysis apparatus according to claim 13, wherein the first position is a swing start position, and the second position is a swing turning position.

15. The motion analysis apparatus according to claim 13, wherein the first position is a swing turning position, and the second position is a hitting position.

16. The motion analysis apparatus according to claim 13, wherein the first position is a hitting position, and the second position is a swing end position.

17. The motion analysis apparatus according to claim 13, wherein the first position is a swing turning position, and the second position is a swing end position.

18. The motion analysis apparatus according to claim 13, wherein the first position is a stoppage position when the swing is started, and the second position is a swing end position.

19. The motion analysis apparatus according to claim 14, wherein the swing width is a length of the swing trajectory from the first position to the second position.

20. A non-transitory storage device storing a motion analysis program that allows a user to gain accuracy of reproducing a swing width of a putter corresponding to a traveled distance of a hit ball by causing a computer to execute:
wirelessly obtaining an output signal from an inertial sensor along a swing trajectory of the putter from an address position to a swing turning position, the swing trajectory having a magnitude corresponding to a putting swing, wherein the inertial sensor comprises an acceleration sensor and a gyro sensor, and the inertial sensor is attached to a shaft of the putter having a hitting surface angled in relation to a longitudinal axis of the putter;
specifying the swing width from the address position to the swing turning position on the swing trajectory on the basis of: (i) a swing position of the putter which is acquired by using the output signal from the inertial sensor, and (ii) a distance from the inertial sensor to a predetermined location along the putter,
displaying the swing width for each swing motion of the putter.

21. The motion analysis method according to claim 1, wherein the processor is further configured to analyze a deviation angle $\theta 1$ between a face surface of the putter during impact with the ball and a virtual vertical plane with respect to a hitting target direction.

22. The motion analysis method according to claim 1, wherein the processor is further configured to analyze a deviation angle $\theta 2$ between a face surface of the putter during impact with the ball and a virtual vertical plane with respect to a tangential direction during impact in contact with a movement trajectory of the face surface.

23. The motion analysis method according to claim 1, wherein the processor is further configured to analyze a deviation amount $\delta$ of a hit point of the ball during impact with the ball relative to a virtual reference position P0 set on a face surface of the putter, on a basis of angular velocity around the shaft.

24. The motion analysis method according to claim 1, wherein the processor is further configured to analyze a deviation angle $\theta 3$ between an inclined angle with respect to a vertical surface of a face surface of the putter during impact with the ball and a reference inclined angle.

25. The motion analysis method according to claim 1, wherein the processor is further configured to analyze a fourth deviation angle $\theta 4$ between a tangential direction during impact with the ball in contact with the movement trajectory of a face surface of the putter projected onto a vertical surface and a target direction projected onto the vertical surface.

* * * * *